(12) United States Patent
    Zada

(10) Patent No.: US 11,039,823 B2
(45) Date of Patent: Jun. 22, 2021

(54) MINIMAL-ACCESS PERCUTANEOUS AND SELF-RETRACTING SURGICAL SYSTEM

(71) Applicant: Z Surgical LLC, Los Angeles, CA (US)

(72) Inventor: Gabriel Zada, Los Angeles, CA (US)

(73) Assignee: Z Surgical LLC, Los Angeles, CA (US)

( * ) Notice: Subject to any disclaimer, the term of this patent is extended or adjusted under 35 U.S.C. 154(b) by 381 days.

(21) Appl. No.: 15/969,176

(22) Filed: May 2, 2018

(65) Prior Publication Data

US 2018/0317899 A1     Nov. 8, 2018

Related U.S. Application Data

(60) Provisional application No. 62/500,813, filed on May 3, 2017.

(51) Int. Cl.
    *A61B 1/00*      (2006.01)
    *A61B 17/02*     (2006.01)
    *A61B 1/05*      (2006.01)
    *A61B 17/29*     (2006.01)
    *A61B 17/32*     (2006.01)
    (Continued)

(52) U.S. Cl.
    CPC ........ *A61B 17/0218* (2013.01); *A61B 1/0055* (2013.01); *A61B 1/00087* (2013.01); *A61B 1/00135* (2013.01); *A61B 1/018* (2013.01); *A61B 1/05* (2013.01); *A61B 17/29* (2013.01); *A61B 17/320016* (2013.01); *A61B 17/3421* (2013.01); *A61B 17/3478* (2013.01); *A61B 1/126* (2013.01); *A61B 17/3201* (2013.01); *A61B 17/3476* (2013.01); *A61B 18/14* (2013.01); *A61B 2017/2215* (2013.01); *A61B 2017/2906* (2013.01); *A61B 2017/320044* (2013.01); *A61B 2017/3447* (2013.01); *A61B 2017/3454* (2013.01); *A61B 2018/00595* (2013.01); *A61B 2217/005* (2013.01)

(58) Field of Classification Search
    None
    See application file for complete search history.

(56) References Cited

U.S. PATENT DOCUMENTS 5,632,717 A * 5/1997 Yoon ................. A61B 1/00082
                                                 600/104
6,352,503 B1 * 3/2002 Matsui ............... A61B 17/1285
                                                 600/104
(Continued)

FOREIGN PATENT DOCUMENTS

| MX | 2013001221     | 7/2014 |
| WO | WO 2004/037097 | 5/2004 |
| WO | WO 2012/051292 | 4/2012 |

OTHER PUBLICATIONS

PCT Search and Report and Written Opinion for international application No. PCT/US2018/030666 dated Jul. 9, 2018.

*Primary Examiner* — Timothy J Neal
(74) *Attorney, Agent, or Firm* — Knobbe, Martens, Olson & Bear, LLP

(57) ABSTRACT

Disclosed herein are embodiments of a minimally-invasive surgical system and methods of use which can mimic a mosquito proboscis to efficiently penetrate tissue. The delivery system can utilize a plurality of modular strut instruments to create a working tissue canopy and apply any number of surgical actions to a target tissue.

28 Claims, 19 Drawing Sheets

(51) Int. Cl.
*A61B 17/34* (2006.01)
*A61B 1/005* (2006.01)
*A61B 1/018* (2006.01)
A61B 18/00 (2006.01)
A61B 18/14 (2006.01)
A61B 17/3201 (2006.01)
A61B 1/12 (2006.01)
A61B 17/221 (2006.01)

(56) References Cited

U.S. PATENT DOCUMENTS

| | | |
|---|---|---|
| 6,537,242 B1 | 3/2003 | Palmer |
| 6,743,211 B1 | 6/2004 | Prausnitz et al. |
| 6,902,554 B2 | 6/2005 | Huttner |
| 7,087,035 B2 | 8/2006 | Trautman et al. |
| 8,128,592 B2 | 3/2012 | Mitelberg et al. |
| 2003/0032975 A1 | 2/2003 | Bonutti |
| 2004/0138529 A1* | 7/2004 | Wiltshire ............ A61B 1/0055 600/144 |
| 2005/0085691 A1* | 4/2005 | Nakao ................ A61B 1/00071 600/128 |
| 2006/0079925 A1* | 4/2006 | Kerr .................. A61B 17/3439 606/198 |
| 2007/0287889 A1* | 12/2007 | Mohr .................... A61B 34/72 600/207 |
| 2011/0257672 A1* | 10/2011 | Friedman ............. A61M 29/00 606/190 |
| 2012/0203137 A1 | 8/2012 | Neuman |
| 2013/0274553 A1* | 10/2013 | Piskun ............... A61B 1/00154 600/114 |
| 2016/0038018 A1 | 2/2016 | Wilson et al. |
| 2016/0038133 A1 | 2/2016 | Smith et al. |
| 2016/0346519 A1 | 12/2016 | Bagwell et al. |

\* cited by examiner

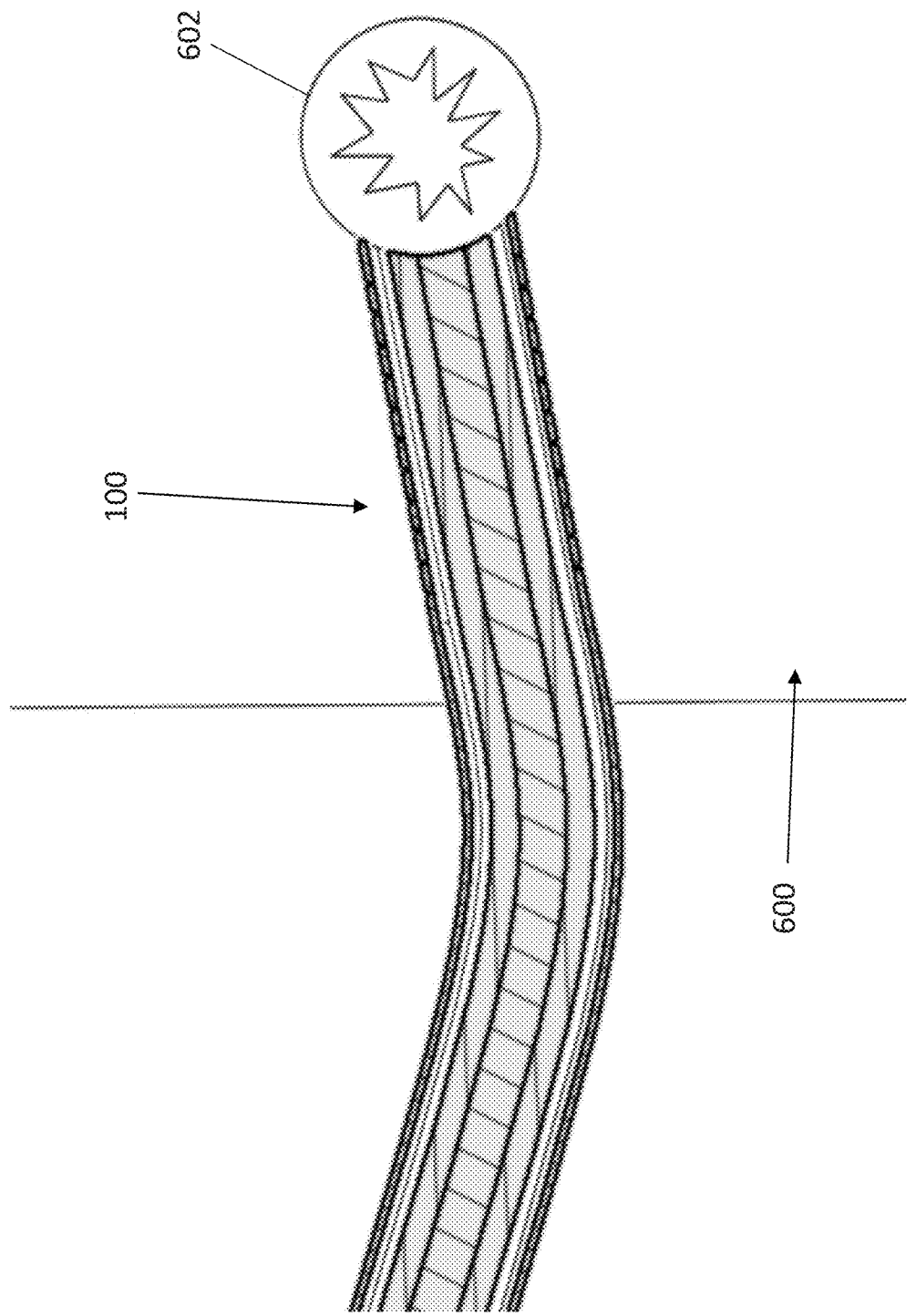

MINIMAL-ACCESS PERCUTANEOUS AND SELF-RETRACTING SURGICAL SYSTEM

INCORPORATION BY REFERENCE TO ANY PRIORITY APPLICATIONS

This Application claims from the benefit of U.S. Application No. 62/500,813, filed May 3, 2017, titled "MINIMAL-ACCESS PERCUTANEOUS AND SELF-RETRACTING SURGICAL SYSTEM," the entirety of which is incorporated herein by reference.

BACKGROUND

Field

Embodiments of the disclosure relate to modular surgical systems and methods of use for performing any of a number of procedures on a target tissue.

Description of the Related Art

Minimally-invasive, robotic, and endoscopic surgery are rapidly evolving disciplines that depend to a significant extent on optical and instrument miniaturization and maneuverability. The ability to perform minimally-invasive operations via increasingly small natural corridors, surgical ports, keyhole approaches, and percutaneous access points is increasing, and remains heavily dependent on existing and emerging technology. An inherent obstacle associated with current working paradigms for surgical target visualization and modular end effector manipulation is the ability to operate within soft tissue, vis-a-vis an air or fluid medium.

SUMMARY OF THE INVENTION

Embodiments of the present disclosure are directed to a surgical systems and devices and methods of use. The present disclosure includes, but is not limited to, the following numbered embodiments.

Embodiment 1

A multi-functional surgical system comprising an outer sheath having a proximal end, a distal end, and a lumen extending between the proximal end and the distal end, an inner module located within the lumen of the outer sheath, the inner module comprising a plurality of lumens extending from a proximal end to a distal end of the inner module, at least one labrum extending through at least one of the plurality of lumens of the inner module and configured to extend out the distal end of the outer sheath, wherein the at least one labrum is configured to penetrate tissue and to move from a radially closed position to a radially open position, and wherein the at least one labrum is configured to withdraw into the inner module, and a plurality of struts, each of the plurality of struts extending through one of the plurality of lumens of the inner module, wherein the plurality of struts are configured to radially expand as they are advanced distally from the distal end of the outer sheath to form a canopy working area and to circumferentially move tissue, wherein at least some of the plurality of struts comprise a surgical end tip having a surgical function.

Embodiment 2

The multi-functional surgical system of Embodiment 1, wherein the outer sheath and the inner module are flexible.

Embodiment 3

The multi-functional surgical system of any one of Embodiments 1-2, further comprising a camera or endoscope extending through one of the plurality of lumens of the inner module.

Embodiment 4

The multi-functional surgical system of any one of Embodiments 1-3, further comprising a hub and relay connected to a processor with a human or robotic interface.

Embodiment 5

The multi-functional surgical system of any one of Embodiments 1-4, further comprising a power source connected to at least one of the surgical end tips.

Embodiment 6

The multi-functional surgical system of any one of Embodiments 1-5, wherein the plurality of struts are configured to form a grasping claw while being withdrawn into the outer sheath.

Embodiment 7

The multi-functional surgical system of any one of Embodiments 1-6, wherein the at least one labrum comprises a pair of legs each having a cutting surface and a needle.

Embodiment 8

The multi-functional surgical system of any one of Embodiments 1-7, wherein the surgical end tips comprise one or more of a micrograsping forcep, a microscissors, a navigation actuator, a microdissector, a cautery instrument, a suction device, a vessel clip, a ligation instrument, a drug delivery device, an ultrasonic or microdoppler flow probe, and a spectroscopy probe.

Embodiment 9

The multi-functional surgical system of any one of Embodiments 1-8, wherein at least a portion of the at least one labrum is configured to vibrate.

Embodiment 10

The multi-functional surgical system of any one of Embodiments 1-9, wherein the system is bendable and steerable.

Embodiment 11

The multi-functional surgical system of any one of Embodiments 1-10, wherein each of the end tips is configured to longitudinally retract and extend within a lumen of one of the plurality of struts.

Embodiment 12

The multi-functional surgical system of any one of Embodiments 1-11, wherein each of the plurality of struts comprises a bend, the bend directing the strut from extending radially outward to extending radially inwards.

Embodiment 13

The multi-functional surgical system of Embodiment 12, wherein the bend comprises a hinge configured to change angles.

Embodiment 14

The multi-functional surgical system of any one of Embodiments 1-13, wherein some of the plurality of struts do not have a surgical end tip.

Embodiment 15

A method of performing surgery comprising advancing a multi-functional surgical system having an outer sheath to a target location with a target tissue, the advancing comprising cutting through tissue with at least one labrum of the surgical system to enter the target location, the at least one labrum extending through a lumen of the outer sheath and out a distal end of the outer sheath, distally advancing a plurality of struts through the outer sheath and into the target location, wherein the plurality of struts radially expand as they are distally advanced out of the outer sheath to form a canopy working area around the target tissue, and wherein at least some of the plurality of struts includes an end effector, and performing an action on the target tissue using at least one of the end effectors of the plurality of struts.

Embodiment 16

The method of Embodiment 15, wherein the performing the action comprises cutting, cauterizing, dissection, clipping, ligation, drug delivery, suction, removal, or grasping.

Embodiment 17

The method of any one of Embodiments 15-16, wherein the surgical system is controlled robotically.

Embodiment 18

The method of any one of Embodiments 15-17, further comprising retracting the at least one labrum into the outer sheath prior to or simultaneously while distally advancing the plurality of struts.

Embodiment 19

The method of any one of Embodiments 15-18, further comprising withdrawing the plurality of struts after performing the action, wherein the withdrawing comprises radially compressing the plurality of struts to grasp the target tissue and translate the target tissue towards the outer sheath.

Embodiment 20

A surgical system comprising an outer sheath, a first plurality of struts positioned within or attached to the outer sheath, the first plurality of struts comprising sharp tips that form a unified tissue dissector, the unified tissue dissector configured to penetrate into tissue and radially open and close to cut and retract tissue radially outwardly to facilitate advancement of the surgical system through soft tissue, and a second plurality of struts configured to be advanced from within the outer sheath, the second plurality of struts expanding radially when distally advanced from the outer sheath to form a retraction canopy around a surgical target site, wherein at least some of the second plurality of struts comprise working instruments configured to perform a function at the surgical target site.

Embodiment 21

The surgical system of Embodiment 20, wherein the second plurality of struts is configured to form a grasping claw when withdrawn into the outer sheath.

Embodiment 22

The surgical system of any one of Embodiments 20-21, further comprising a hub and relay to connect one or more struts to a processor and human or robotic interface.

Embodiment 23

The surgical system of any one of Embodiments 20-22, wherein the first plurality of struts comprises a pair of labrums and an inner needle.

Embodiment 24

The surgical system of Embodiment 23, wherein the second plurality of struts comprise strut instruments interspersed with the pair of labrums and inner needle.

Embodiment 25

The surgical system of any one of Embodiments 20-24, wherein the unified tissue dissector is configured to retract tissue as the outer sheath docks proximal to the surgical site.

Embodiment 26

The surgical system of any one of Embodiments 20-25, wherein the second plurality of struts are configured to advance from within the outer sheath as the tissue dissector is withdrawn into the outer sheath.

Embodiment 27

The surgical system of any one of Embodiments 20-26, further comprising a camera or endoscope positionable within the outer flexible sheath.

Embodiment 28

The surgical system of any one of Embodiments 20-27, wherein the working instruments comprise one or more a micrograsping forceps, a microscissors, a microdissector, a cautery instrument, a suction device, a vessel clip, a ligation instrument, a drug delivery device, an ultrasonic or microdoppler flow probe, and a spectroscopy probe.

Embodiment 29

The surgical system of any one of Embodiments 20-28, further comprising a power source connected to at least one of the working instruments.

Embodiment 30

The surgical system of any one of Embodiments 20-29, wherein the first plurality of struts comprises a pair of legs and a needle.

Embodiment 31

The surgical system of any one of Embodiments 20-30, wherein at least a portion of the tissue dissector is configured to vibrate.

Embodiment 32

The surgical system of any one of Embodiments 20-31, wherein the outer sheath is bendable and steerable.

Embodiment 33

The surgical system of any one of Embodiments 20-32, wherein each of the working instruments is configured to longitudinally retract and extend within a lumen of one of the second plurality of struts.

Embodiment 34

The surgical system of any one of Embodiments 20-33, wherein each of the second plurality of struts comprises a bend, the bend directing the struts from extending radially outward to extending radially inwards.

Embodiment 35

The surgical system of Embodiment 34, wherein the bend comprises a hinge configured to change angles.

Embodiment 36

The surgical system of any one of Embodiments 20-35, wherein some of the second plurality of struts do not have working instrument.

Embodiment 37

The surgical system of any one of Embodiments 20-36, wherein the first plurality of struts are configured to cut and retract tissue radially outwards to facilitate advancement of the system through tissue.

Embodiment 38

A method of using the surgical system of any one of Embodiments 20-37, the method comprising advancing the surgical system to a target location within a target tissue, the advancing comprising cutting through tissue with the tissue dissector to enter the target location, distally advancing the second plurality of struts through the outer sheath and into the target location, where the second plurality of struts radially expand as they are distally advanced out of the outer sheath to form the retraction canopy around the target tissue, and performing the function on the target tissue using the working instruments.

Embodiment 39

An assembly for a surgical system, the assembly comprising a first surgical device comprising at least one labrum at a distal end configured to penetrate tissue and to move from a radially closed position to a radially open position, and a second surgical device comprising a plurality of struts, each of the plurality of struts being configured to radially expand as they are advanced distally to form a canopy working area, wherein at least some of the plurality of inner struts comprise an end tip having surgical functionality.

Embodiment 40

The method of Embodiment 39, the method comprising advancing the first surgical device near to a target tissue to form a tunnel, withdrawing the first surgical device through the tunnel, advancing the second surgical device through the tunnel, distally and radially extending the plurality of struts of the second surgical device to form the canopy working area, and performing a surgical operation with at least one of the end tips.

Embodiment 41

A surgical system comprising an outer flexible sheath, a first plurality of struts positioned within or attached to the outer flexible sheath, the first plurality of struts having sharp tips that together form a unified tissue dissector, the tissue dissector having an advanced position for penetrating into tissue and a retracted position in which the first plurality of struts are configured to retract tissue radially outwardly, and a second plurality of struts advanceable from within the outer flexible sheath, the second plurality of struts being expandable radially when advanced from the outer flexible sheath to form a canopy around a surgical site, wherein at least some of the second plurality of struts comprise working instruments configured to perform a function at the surgical site.

Embodiment 42

The surgical system of Embodiment 41, wherein the second plurality of struts is configured to form a grasping claw when withdrawn into the outer sheath.

Embodiment 43

The surgical system of any one of Embodiments 41-42, further comprising a hub and relay to connect one or more struts to a processor and human or robotic interface.

Embodiment 44

The surgical system of any one of Embodiments 41-43, wherein the first plurality of struts comprises a pair of labrums and an inner needle.

Embodiment 45

The surgical system of Embodiment 44, wherein the second plurality of struts comprise strut instruments interspersed with the pair of labrums and inner needle.

Embodiment 46

The surgical system of any one of Embodiments 41-45, wherein the unified tissue dissector is configured to retract tissue as the outer sheath docks proximal to the surgical site.

Embodiment 47

The surgical system of any one of Embodiments 41-46, wherein the second plurality of struts are configured to advance from within the outer sheath as the tissue dissector is withdrawn into the outer sheath.

Embodiment 48

The surgical system of any one of Embodiments 41-47, further comprising a camera or endoscope positionable within the outer flexible sheath.

Embodiment 49

The surgical system of any one of Embodiments 41-48, wherein the working instruments comprise one or more a micrograsping forceps, a microscissors, a microdissector, a cautery instrument, a suction device, a vessel clip, a ligation instrument, a drug delivery device, an ultrasonic or microdoppler flow probe, and a spectroscopy probe.

Embodiment 50

The surgical system of any one of Embodiments 41-49, further comprising a power source connected to at least one of the working instruments.

Embodiment 51

The surgical system of any one of Embodiments 41-50, wherein the first plurality of struts comprises a pair of legs and a needle.

Embodiment 52

The surgical system of any one of Embodiments 41-51, wherein at least a portion of the tissue dissector is configured to vibrate.

Embodiment 53

The surgical system of any one of Embodiments 41-52, wherein the outer sheath is bendable and steerable.

Embodiment 54

The surgical system of any one of Embodiments 41-53, wherein each of the working instruments is configured to longitudinally retract and extend within a lumen of one of the second plurality of struts.

Embodiment 55

The surgical system of any one of Embodiments 41-54, wherein each of the second plurality of struts comprises a bend, the bend directing the struts from extending radially outward to extending radially inwards.

Embodiment 56

The surgical system of Embodiment 55, wherein the bend comprises a hinge configured to change angles.

Embodiment 57

The surgical system of any one of Embodiments 41-56, wherein some of the second plurality of struts do not have working instrument.

Embodiment 58

The surgical system of any one of Embodiments 41-57, wherein the first plurality of struts are configured to cut and retract tissue radially outwards to facilitate advancement of the system through tissue.

Embodiment 59

A method of using the surgical system of any one of Embodiment 41-58, the method comprising advancing the surgical system to a target location within a target tissue, the advancing comprising cutting through tissue with the tissue dissector to enter the target location, distally advancing the second plurality of struts through the outer sheath and into the target location, where the second plurality of struts radially expand as they are distally advanced out of the outer sheath to form the retraction canopy around the target tissue, and performing the function on the target tissue using the working instruments.

BRIEF DESCRIPTION OF THE DRAWINGS

FIGS. 12-18 illustrate an example method of use of an embodiment of the disclosed surgical device.

DETAILED DESCRIPTION

Disclosed herein are embodiments of minimally-invasive devices, systems and methods to facilitate a number of operations located throughout the body based on principles derived from and designed to mimic a mosquito proboscis targeting a blood vessel, adapted to facilitate access to a surgical target for any number of surgical indications. Specifically, embodiments described herein are directed to a device and system designed to access a surgical target and operate within the human body in a soft tissue, air or fluid medium. The device and system may comprise a variety of interchangeable, modular instruments and provide targeted, minimally-invasive access and visualization via a circumferential retractor and dissector. The dissector may mimic a mosquito proboscis, thus accessing a target site while minimally disrupting tissue along the way. Further, the retraction can maximize visualization and workplace clearance for operating.

Embodiments of the device may be used to 1) achieve percutaneous or minimally-invasive "keyhole" access, 2) maneuver towards a surgical target with minimal tissue disruption through a soft tissue, air or fluid medium, 3) dilate and circumferentially retract soft tissue proximal to the surgical target to improve visualization and surgical manipulation, and 4) perform a number of surgical maneuvers including cutting, grasping, cautery, tissue resection/biopsy, ligation, clipping, and drug delivery, among others.

Figure 1:
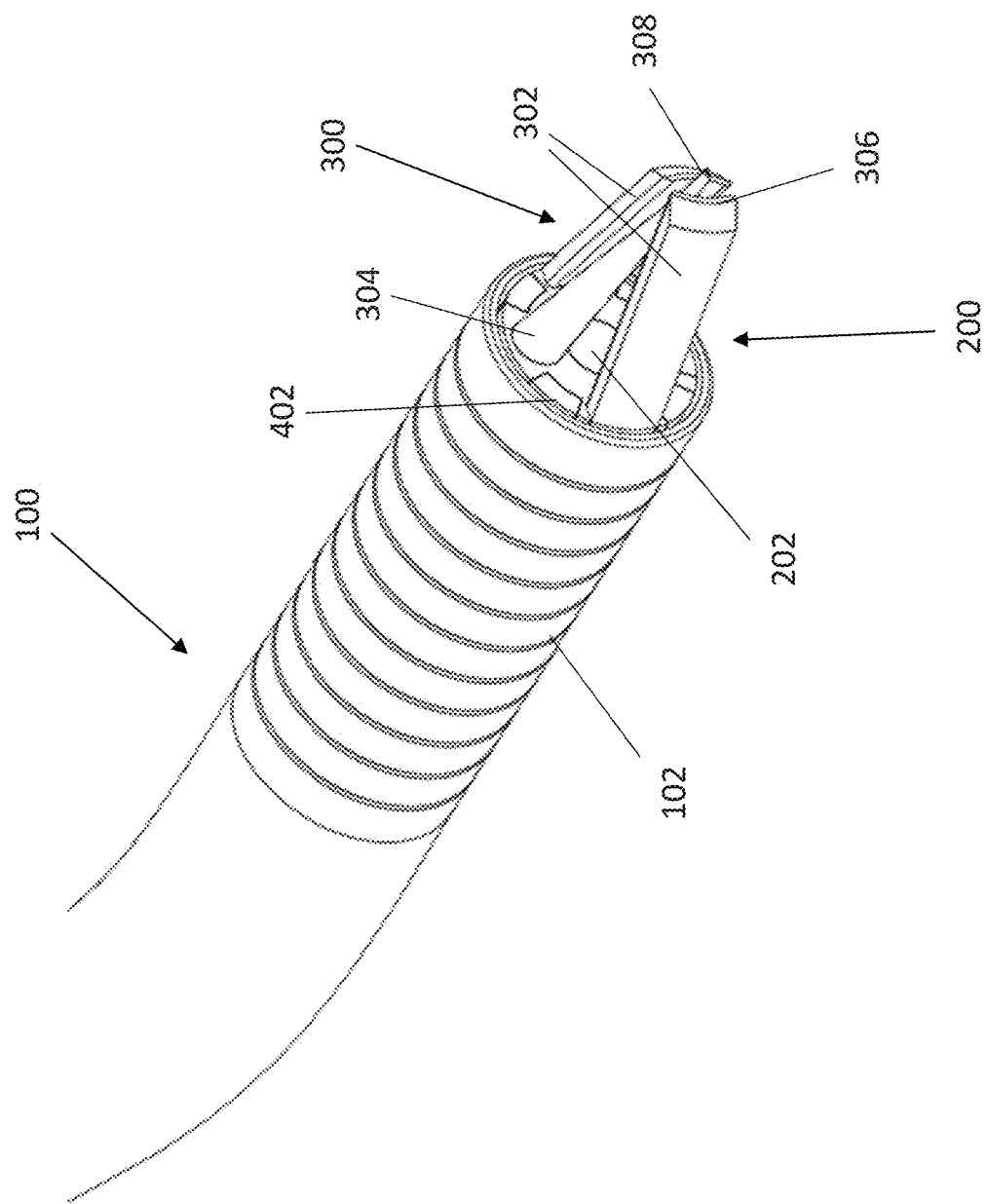
FIG. 1 illustrates an embodiment of the surgical device with the labrum in a radially closed position.

FIG. 1 illustrates an embodiment of the surgical device (e.g., surgical system, system, assembly, or device) 100. As shown, the device 100 can include an outer sheath 102 configured for maneuvering in tissues, such as in tissue of a patient. In some embodiments, the outer sheath 102 may be a flexible. In some embodiments, the outer sheath 102 may be semi-rigid. In some embodiments, the outer sheath 102 may be rigid. The particular rigidity does not limit the disclosure. In some embodiments, the outer sheath 102 can be straight. In some embodiments, the outer sheath 102 may be curved. In some embodiments, the outer sheath 102 may have one or more curves. The outer sheath 102 may be metal (such as aluminum, titanium, Nitinol), plastic, rubber, etc. and the material does not limit the disclosure. The outer sheath may be biocompatible.

In some embodiments, the outer sheath 102 may have an outer diameter of 15, 14, 13, 12, 11, 10, 9, 8, 7, 6, or 5 mm. In some embodiments, the outer sheath 102 may have an outer diameter of greater than 15, 14, 13, 12, 11, 10, 9, 8, 7, 6, or 5 mm. In some embodiments, the outer sheath 102 may have an outer diameter of less than 15, 14, 13, 12, 11, 10, 9, 8, 7, 6, or 5 mm. In some embodiments, the outer sheath 102 may have an inner diameter of 15, 14, 13, 12, 11, 10, 9, 8, 7, 6, or 5 mm. In some embodiments, the outer sheath 102 may have an inner diameter of greater than 15, 14, 13, 12, 11, 10, 9, 8, 7, 6, or 5 mm. In some embodiments, the outer sheath 102 may have an inner diameter of less than 15, 14, 13, 12, 11, 10, 9, 8, 7, 6, or 5 mm. The outer sheath 102 may have a lumen extending longitudinally through it from a proximal end (e.g., near the operator) to the distal end (e.g., the end portion shown in FIG. 1).

In some embodiments, the device 100 may have a length of about 10, 11, 12, 13, 14, 15, 16, 17, 18, 19, or 20 cm. In some embodiments, the device 100 may have a length of greater than about 10, 11, 12, 13, 14, 15, 16, 17, 18, 19, or 20 cm. In some embodiments, the device 100 may have a length of less than about 10, 11, 12, 13, 14, 15, 16, 17, 18, 19, or 20 cm.

In some embodiments, the device 100 may have a length of 10, 20, 30, 40, 50, 60, 70, 80, 90, or 100 cm. In some embodiments, the device 100 may have a length of greater than 10, 20, 30, 40, 50, 60, 70, 80, 90, or 100 cm. In some embodiments, the device 100 may have a length of less than 10, 20, 30, 40, 50, 60, 70, 80, 90, or 100 cm.

Within the lumen, the device 100 may include an inner module 200. In some embodiments, the device 100 may not include an inner module. The inner module 200 can be concentrically aligned within the lumen of the outer sheath 102 to fit within and pass through the outer sheath 102. In some embodiments, the inner module 200 may have an outer diameter of 15, 14, 13, 12, 11, 10, 9, 8, 7, 6, or 5 mm. In some embodiments, the inner module 200 may have an outer diameter of greater than 15, 14, 13, 12, 11, 10, 9, 8, 7, 6, or 5 mm. In some embodiments, the inner module 200 may have an outer diameter of less than 15, 14, 13, 12, 11, 10, 9, 8, 7, 6, or 5 mm. The inner module 200 outer surface may abut the inner surface of the outer sheath 102. The inner module 200 may be attached to an inner surface of the outer sheath 102. In some embodiments, the inner module 200 can translate relative to the outer sheath 102. In some embodiments, the inner module 200 stays connected to the outer sheath 102. The inner module 200 may contain a number of lumens extending through which hold the different components discussed below. The lumens may extend from a distal end to a proximal end of the inner module 200. The inner module 200 may extend the entire length of the device 100. In some embodiments, the inner module 200 may extend less than the entire length of the device 100. The inner module 200 may be a flexible casing. The inner module 200 may be made of a flexible material so as to bend with the device 100 and prevent any damage to the components within the inner module 200. The inner module 200 may be plastic, polymer, rubber, metal, and the type of material is not limiting.

The inner module 200 may contain a number of different components, such as disclosed herein. In some embodiments, all of the below-listed components are included. In some embodiments, only some of the below-listed components are used.

In some embodiments, the inner module 200 can include one or more flexible suction cannulae (for example 2 mm diameter). In some embodiments, the inner module 200 can include a proximally situated hub or port for electrical wiring (for example 2 mm diameter). In some embodiments, the inner module 200 can include a port for irrigation or drug delivery (for example 1 mm diameter). In some embodiments, the inner module 200 can include a fiberoptic light source. In some embodiments, the inner module 200 can include a distal end (actuator) designed to interface with currently existing navigation, stereotactic, or robotic interfaces to provide the end user with information pertaining to the location of the distal end on an imaging study (for example 1 mm diameter). In some embodiments, the inner module 200 can include an ultrasonic probe or camera (for example 2 mm diameter). Any, some, or all of the above listed components can be included in the device 100.

In some embodiments, the inner module 200 may include a camera/flexible endoscope/visualization device 202. The visualization device 202 can include, for example, a lens/aperture. This visualization device 202 can be used to provide an operator a view of the distal end of the device 200 at an externally located monitor (e.g., computer screen, laptop, smart phone). The visualization device 202 may be directly connected to an externally located monitor and/or power source. The visualization device 202 may be wirelessly connected to an externally located monitor and/or power source. In some embodiments, the visualization device 202 can be flexible, semi-rigid, or rigid. As shown, the visualization device 202 can extend through the lumen of the outer sheath 102. In some embodiments, the visualization device 202 can extend fully or partially the length of the outer sheath 102. In some embodiments, the visualization device 202 can have a diameter of 5, 4, 3, 2, or 1 mm. In some embodiments, the visualization device 202 can have a diameter of larger than 5, 4, 3, 2, or 1 mm. In some embodiments, the visualization device 202 can have a diameter of smaller than 5, 4, 3, 2, or 1 mm. In some embodiments, the device 100 may not include a visualization device 202. In some embodiments, the visualization device 202 can extend the full length of the device 100. In some embodiments, the visualization device 202 may extend distal the outer sheath 102. In some embodiments, the visualization device 202 may be recessed proximal to the distal end of the outer sheath 102. In some embodiments, the visualization device 202 can be steered, thereby steering the device 100. In some embodiments, the visualization device 202 can have an adjacent micro-irrigation port (such as extending through the inner module 200) to provide irrigation of the lens if it should become obscured due to surgical byproducts such as blood, smoke, tissue or fluid.

In some embodiments, the outer sheath 102 may be actively steered by a user or a robotic interface. In some embodiments, the outer sheath may be passively driven by steering of another portion of the device. For example, the visualization device 202 may be steered in some embodiments. In some embodiments, the inner module 200 may be steered. The outer sheath 102 may experience 1, 2, 3, 4, 5, or 6 bends during steering.

In some embodiments, the inner module 200 can include a labrum (e.g., tissue dissector, proboscis, first plurality of struts) 300. The labrum 300 can be advantageous for penetrating tissue, specifically for making a minimal-access percutaneous insertion of the device 100 and continued advancement through tissue. Thus, the labrum 300 can generally reduce damage to the patient when inserting and maneuvering the device 100. For example, the labrum 300 can be designed to penetrate skin and/or soft tissue such as brain, muscle, fat, lung, liver, etc. while causing limited damage.

The labrum 300 can in some embodiments comprise a pair of legs 302 and a needle 304 (e.g., collectively a first plurality of struts), as shown in FIG. 1, each extending through separate (or the same) lumens in the inner module 200. In some embodiments, the labrum 300 can include only one of pair of legs 302 (e.g., each leg can be a labrum and thus the pair of legs 302 can be a pair of labrums) or the needle 304. In some embodiments, the labrum 300 can collectively include the pair of legs 302 and the needle 304. In some embodiments, the labrum 300 can collectively include the pair of legs 302. The legs 302 and needle 304 can have sharp tips that together (either just the pair of legs 302 or the pair of legs 302 with the needle 304) form a unified tissue dissector in some embodiments. The legs 302 can include a cutting edge 306 at their distal end. The cutting edge 306 can be curved in some embodiments. The cutting edge 306 can be straight in some embodiments. The legs 302 can be generally shaped like a rectangular prism, though the particular shape of the legs 302 are not limiting. The needle 304 can include a distal tip 308. In some embodiments, the needle 304 can come to a point. In some embodiments, the needle 304 can include a dual bevel. In some embodiments, the needle 304 can be hollow. In some embodiments, the needle 304 can extend further distally than the legs 302, and thus act as the initial cut/penetration point when advancing the device 100. In some embodiments, the needle 304 may not be used. In some embodiments, three legs 302 can be used where one leg can replace the needle 304. In some embodiments, one leg 304 may be used with the needle 304. In some embodiments, 3, 4, 5, or 6 legs can be used.

The labrum 300 (e.g., the legs 302 and the needle 304) can be configured to radially open and close in some embodiments. Thus, the labrum 300 may be configured to retract tissue radially outwards as the labrum 300 radially opens. In some embodiments, the legs 302 and/or the needle 304 may have straight or serrated side edges for cutting through tissues.

In some embodiments, the labrum 300 can longitudinally retract and extend from the inner module 200 and/or the outer sheath 102. In some embodiments, the labrum 300 can both radially open and close and can longitudinally retract and extend.

When advanced, the labrum 300 can facilitate maneuverability and navigable docking of the outer sheath 102 edge on a surgical target, that may be visualized via a camera or endoscope (such as visualization device 202) on the distal end and possibly predetermined or preplanned on imaging studies correlated to the navigation system and a distal end actuator to provide 3D stereotactic location data, or via ultrasonic or Doppler flow probe guidance to target blood vessels. The labrum 300 may also be equipped with individual actuators or sensors to relay three-dimensional stereotactic information pertaining to instrument tip location and function to a processor or robot located outside the body.

Figure 2:
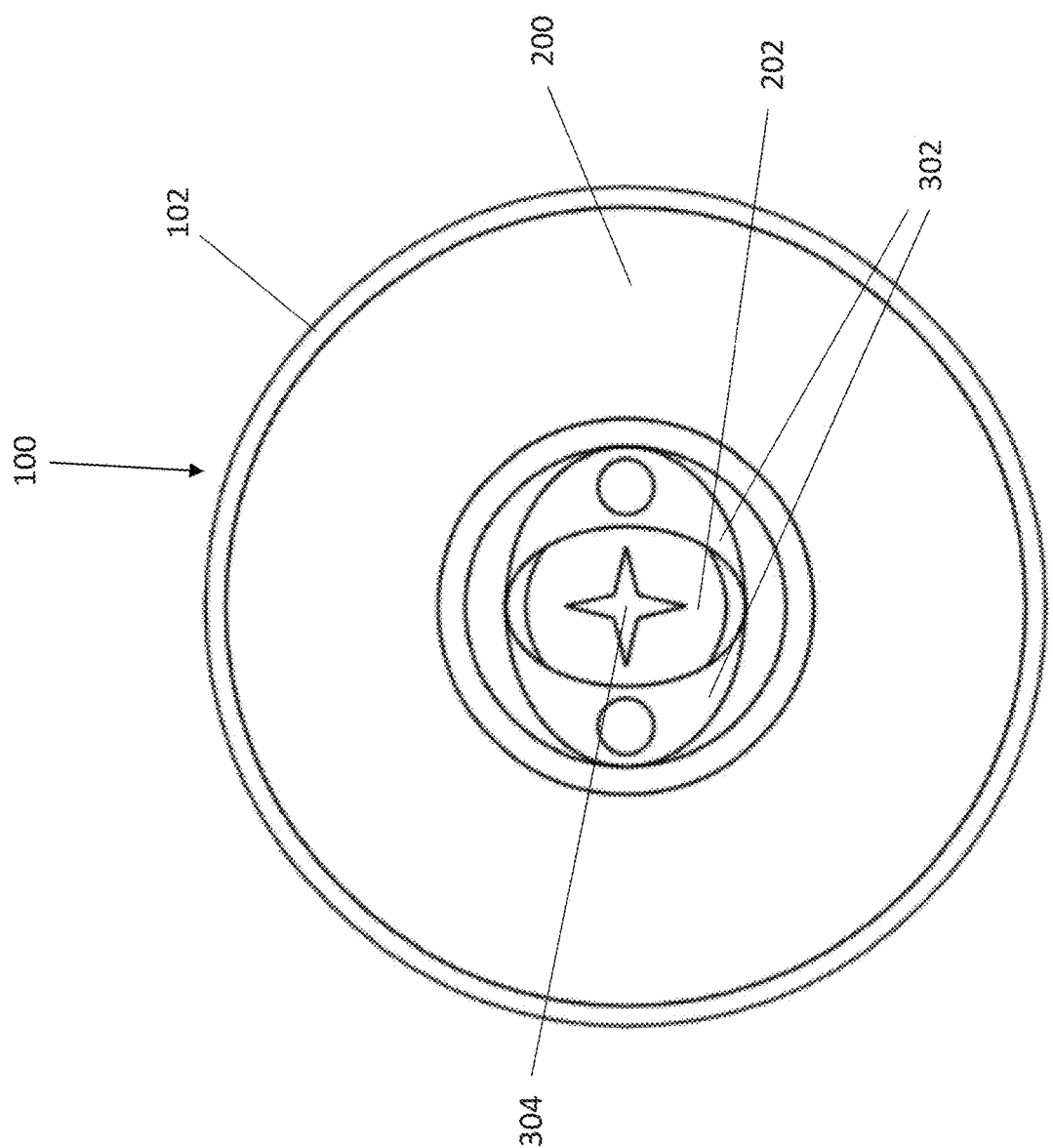
FIG. 2 illustrates a schematic head-on view of an embodiment of the surgical device with the labrum in a radially closed position and with certain structurers omitted for convenience.

FIG. 2 illustrates a schematic example of device 100 showing relative distalmost positions of certain components within the device 100. Certain structural elements (and portions of other shown structural elements) are omitted for convenience. Thus, the particular shape of the device 100 and related components shown in FIG. 2 is not limiting.

FIG. 2 shows a distal end of the device 100 when the labrum 300 is in the radially closed position. As shown, the needle 304 can be generally at the center of the lumen of the outer sheath 102. The two legs 302 can be located on opposite sides of the needle 304. In some embodiments, the needle 304 and legs 302 extend longitudinally straight out of the outer sheath 102 such as shown in FIG. 2. In some embodiments, the needle 304 and legs 302 can extend out of the sheath 102 at an angle and meet generally at the center of the diameter of the outer sheath 102, such as shown in FIG. 1. For example, the needle 304 can extend from a top portion of the outer sheath 102 and the legs can extend from the left and right portions of the outer sheath 102. In some embodiments, the needle 304 and the legs 302 are spaced approximately 60° apart. When the labrum 300 is in the radially closed position, the visualization device 202 may be partially blocked by the needle 304, the legs 302, or both for a user.

Figure 3:
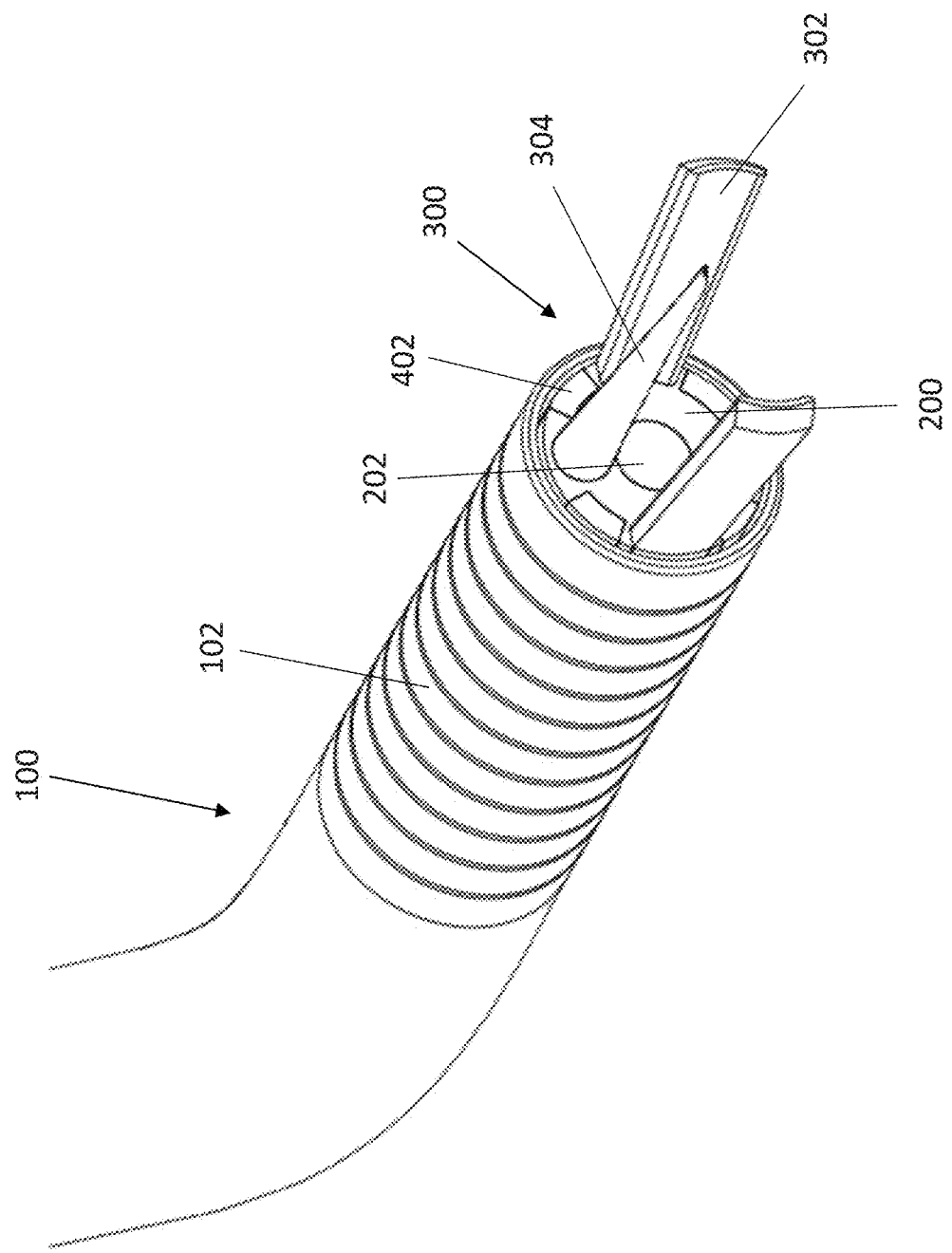
FIG. 3 illustrates an embodiment of the surgical device with the labrum in a radially open position.

FIG. 3 shows the device 100 having the labrum 300 in the radially open position. As shown, the needle 304 and the legs 302 radially rotates outwards (e.g., from the center of the outer sheath 102 towards the edges). In some embodiments, the needle 304 and the legs 302 extend generally straight in the radially open position. In some embodiments, the needle 304 and the legs 302 extend at an outward angle from the center of the outer sheath 102. When the labrum 300 is in the radially open position, the visualization device 202 may be unblocked for a user.

In some embodiments, the needle 304 and the legs 302 can be collectively moved between the radially open and radially closed position. In some embodiments, the needle 304 and the legs 302 can be independently moved between the radially open and the radially closed position. This radial opening and closing can allow for the labrum 300 to cut through tissues as the device 100 moves forward in tissue. For example, the radially opening can spread tissue, and the legs 302 can include sharp edges or serrated edges to cut through the tissue, allowing the device 100 to advance. Further, in some embodiments, the labrum 300 (for example the legs 302 and/or the needle 304) can vibrate, which can improve the cutting through the tissue. In some embodiments, the labrum 300 is constantly radially opening and closing as the device 100 is advanced. The labrum 300 can have an advanced position for penetrating tissue (e.g., the closed position) and a radially expanded position in which the labrum 300 is configured to cut and retract tissue radially outwardly to facilitate advancement of the device 100 through soft tissue.

The labrum 300 can be longitudinally retracted/extended in some embodiments. FIGS. 1 and 3 illustrate the labrum 300 in the longitudinally extended position so that the labrum 300 extends distally from the outer sheath 102. The labrum 300 can then be longitudinally retracted into the outer sheath 102. In some embodiments, the labrum 300 can fully enter the outer sheath 102 upon retraction. In some embodiments, a portion of the labrum 300 can still extend from the distal end of the outer sheath 102 after retraction.

In some embodiments, the needle 304 and the legs 302 can be individually collectively retracted/extended. In some embodiments, the needle 304 and the legs 302 can be independently longitudinally retracted/extended.

While the above discusses the legs 302 and needle 304 located within the inner module 200, in some embodiments, the legs 302 and needle 304 may be attached to the outer sheath 102 (such as at an inner circumference or an outer circumference).

The inner module 200 can further comprise a plurality of struts (e.g., strut instruments, arms, legs, canopy portions, second plurality of struts) that can be longitudinally retracted into the outer sheath 102 and longitudinally extended distal the outer sheath 102. FIGS. 1 and 3 show the struts retracted into the inner module 200 and FIGS. 4-7 illustrate the struts extended longitudinally outwards. The struts can be fully retracted into the inner module 200 and/or outer sheath 102 in some embodiments.

Figure 4:
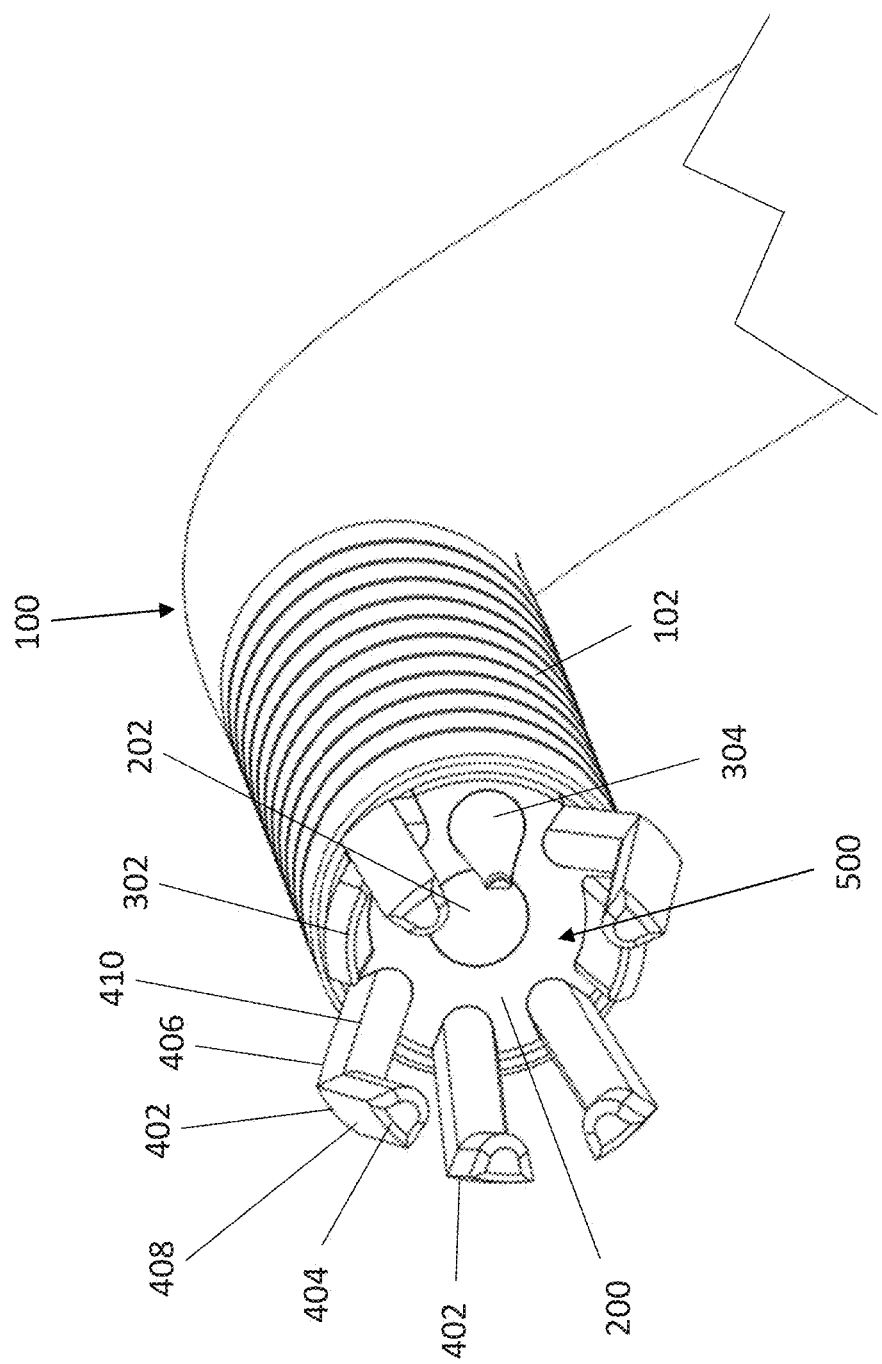
FIG. 4 illustrates an embodiment of the surgical device with the labrum longitudinally retracted and the struts longitudinally extended to form a canopy.

As shown in FIG. 4, the struts 402 can end at a distal tip 404. The distal tip 404 may be atraumatic in some embodiments. The distal tip 404 may have a cutting surface in some embodiments. The distal tip 404 may have a gripping surface in some embodiments. Further, the needle 304 and legs 302 are shown to be withdrawn at least partially into the inner module 200. The struts 402 can extend from an outer circumference of the inner module 200, for example through lumens longitudinally extending through the inner module 200. The struts 402 can be expandable, hinged, and rigid or semi-rigid in some embodiments.

The number of struts 402 extending from the inner module 200 can vary. For example, 1, 2, 3, 4, 5, 6, 7, 8, 9, or 10 struts 402 can be used. In some embodiments, greater than 1, 2, 3, 4, 5, 6, 7, 8, 9, or 10 struts 402 can be used. In some embodiments, less than 2, 3, 4, 5, 6, 7, 8, 9, or 10 struts 402 can be used. In some embodiments, the device 100 can contain 6-8 instruments. In some embodiments, the device 100 can contain 3-5 instruments.

In some embodiments, the struts 402 may all be identical (or generally identical) in size/shape. In some embodiments, the struts 402 may vary in shape. In some embodiments, every other strut 402 may have a different shape. In some embodiments, half of the struts 402 may have one particular shape and half may have a different shape. In some embodiments, all of the struts 402 can extend the same longitudinal distance out of the inner module 200. In some embodiments, some struts 402 may extend a different longitudinal distance than other struts 402. In some embodiments, the struts 402 can be individually extended. In some embodiments, the struts 402 are collectively extended at the same time. In some embodiments, the longitudinal distance of the struts 402 can be varied by a user.

Figure 5:
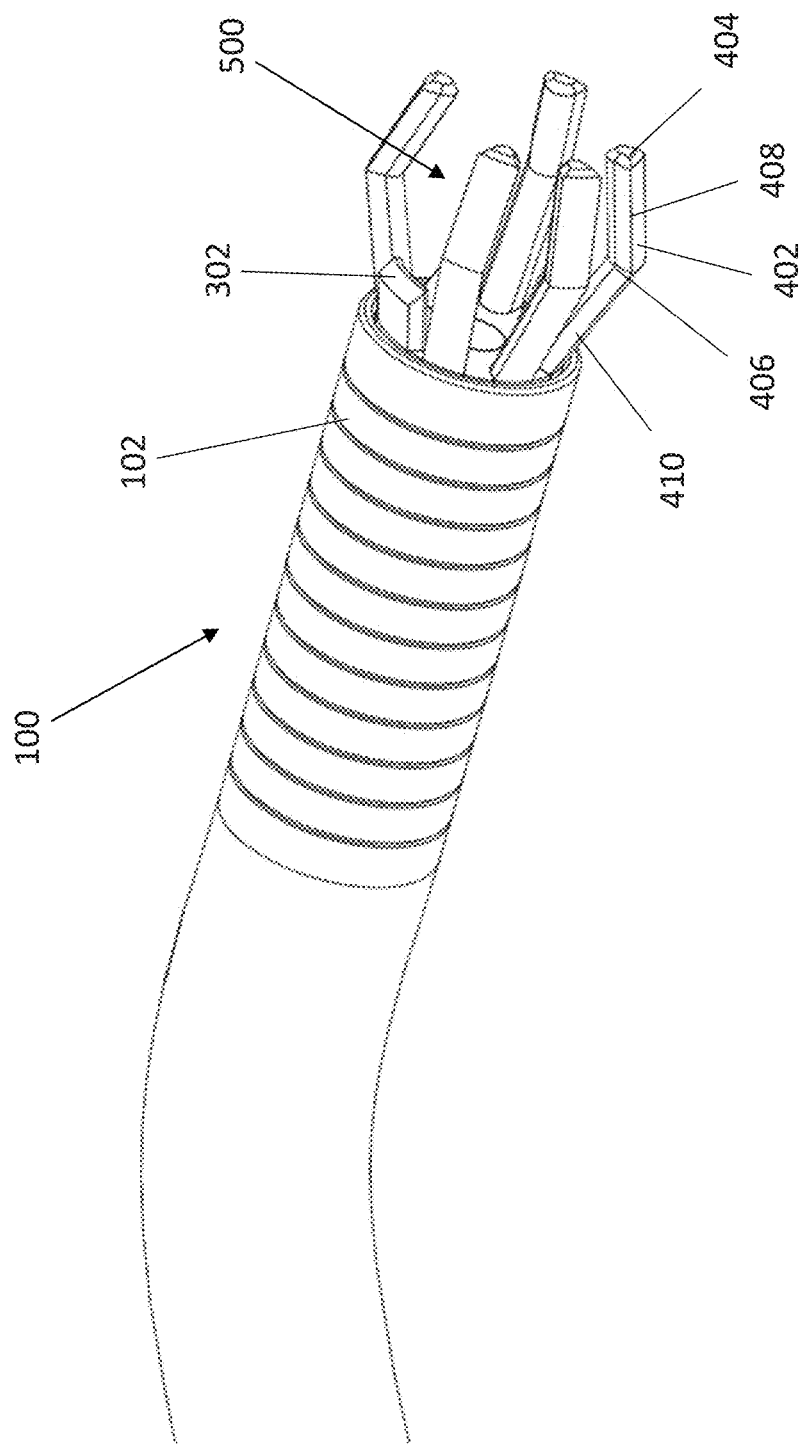
FIG. 5 illustrates an embodiment of the surgical device with the labrum longitudinally retracted and the struts longitudinally extended to form a canopy.

As shown in FIGS. 4-5, the struts 402 can extend from the inner module 200 at an outward angle (e.g., towards the outer sheath 102). Further, the struts 402 may include a bend 406 (e.g., elbow, hinge, curve, angle) to direct the distal tips 404 of the struts 402 outwards radially yet longitudinally aligned with the longitudinal axis of the outer sheath 102 or can be angled inwards towards the center of the outer sheath 102. The bend 406 can help form the canopy discussed below.

In some embodiments, the struts 402 can extend from the inner module 200, as compared to a longitudinal axis of the outer sheath 102, at 25, 30, 35, 40, 45, or 50° angle. In some embodiments, the struts 402 can extend from the inner module 200, as compared to a longitudinal axis of the outer sheath 102, at greater than a 25, 30, 35, 40, 45, or 50° angle. In some embodiments, the struts 402 can extend from the inner module 200, as compared to a longitudinal axis of the outer sheath 102, at less than a 25, 30, 35, 40, 45, or 50° angle. In some embodiments, the struts 402 may have a variable angle extending from the inner module 200 as manipulated by a user.

In some embodiments, the bend or hinge 406 can provide for a 25, 30, 35, 40, 45, or 50° angle between a distal portion 408 and proximal portion 410 of the strut 402. In some embodiments, the bend 406 can provide for greater than a 25, 30, 35, 40, 45, or 50° angle between a distal portion 408 and proximal portion 410 of the strut 402. In some embodiments, the bend 406 can provide for a less than 25, 30, 35, 40, 45, or 50° angle between a distal portion 408 and proximal portion 410 of the strut 402. In some embodiments, the bend 406 can be manipulated by a user in order to change the angle between the distal portion 408 and the proximal portion 410.

In some embodiments, the struts 402 may be curved, angled, or straight and may be rigid, semi-rigid, or hinged. In some embodiments, the struts 402 may be straight while within lumens in the inner module 200, and may bend once extending distally from the inner module 200. In some embodiments, the angles in the struts 402 can be hinges. In some embodiments, the hinges may be manually or robotically operated. In some embodiments, the struts 402 may be made of a memory saving material, so that the struts 402 move to a particular configuration upon distal extension from the inner module 200. In some embodiments, the struts 402 are compressed in a straight configuration in the inner module 200.

The radially outward angle of the struts 402 along with the bends 406 allow for the formation of a working area, work space, retraction canopy, or canopy working area 500. Specifically, by having the struts 402 extend radially outwards from the inner module 200 and then bend back inwards, the struts 402 can push tissue radially away (e.g., retracting tissue out of the way). Thus forms the canopy 500, which is an area where soft tissue has been displaced. This allows for a working space for the end effectors of the struts 402, discussed below, along with improved visualization.

The canopy 500 can be formed within tissue, such as within soft tissue. This can include, for example, organs, skin, muscle, etc. Thus, the device 100 is not limited to just stretching skin at an outer surface of a patient. The canopy 500 can extend proximal to a surgical target, thus retracting tissue out of the way of the surgical target site. This can allow for a user to achieve target visualization and provide a working space. In some embodiments, when the struts 402 are fully advanced and radially expanded, the working diameter of the canopy 500 can be larger than the outer sheath 102 or inner module 202. In some embodiments, the working diameter of the expanded canopy 500 can be 10, 11, 12, 13, 14, or 15 mm. In some embodiments, the working diameter of the expanded canopy 500 can be greater than 10, 11, 12, 13, 14, or 15 mm. In some embodiments, the working diameter of the expanded canopy 500 can be less than 10, 11, 12, 13, 14, or 15 mm. The canopy 500 can simultaneously shield the surgical target site from tissue prolapse, settling, and/or blood products, thereby maintaining visualization and access to the surgical target site.

Figure 6:
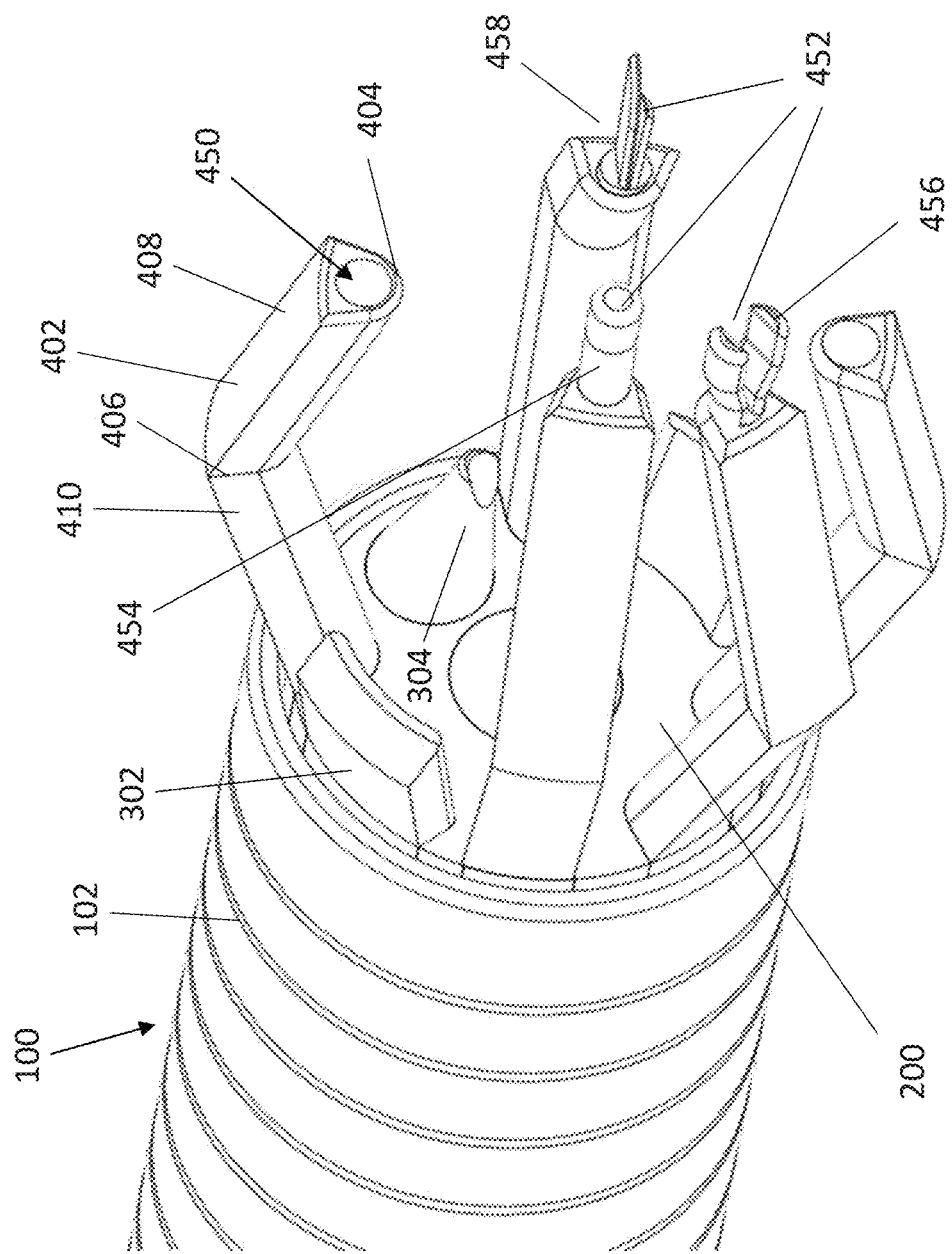
FIG. 6 illustrates an embodiment of the end effectors of the struts distally extended.

FIG. 6 illustrates a closer view of a distal end of the device 100. As shown, the struts 402 can include lumens 450 extending through the struts and out the distal tips 404. The lumens 450 can hold surgical instruments (working instruments, surgical end tips, end tips, micro-instruments, end effectors, etc.) 452. Thus, the surgical instruments 452 can be longitudinally retracted into the struts 402 and can be longitudinally extended distally out of the struts 402. Thus, the surgical instruments 452 can operate in a self-retracting manner. The surgical instruments 452 may be modular or interchangeable. In some embodiments, the surgical instruments 452 can have a diameter of about 0.5, 1, 1.5, 2, 2.5, or 3 mm in diameter. In some embodiments, the surgical instruments 452 can have a diameter of greater than about 0.5, 1, 1.5, 2, 2.5, or 3 mm in diameter. In some embodiments, the surgical instruments 452 can have a diameter of less than about 0.5, 1, 1.5, 2, 2.5, or 3 mm in diameter. In some embodiments, the surgical instruments 452 can work in unison. In some embodiments, the surgical instruments 452 can work independently. The surgical instruments 452 can converge on a surgical target located near the center of the struts distal ends 404.

In some embodiments, the surgical instruments 452 can extend distally 5, 6, 7, 8, 9, 10, 11, 12, 13, 14, or 15 mm from a distal end of the outer sheath 102. In some embodiments, the surgical instruments 452 can extend distally greater than 5, 6, 7, 8, 9, 10, 11, 12, 13, 14, or 15 mm from a distal end of the outer sheath 102. In some embodiments, the surgical instruments 452 can extend distally less than 5, 6, 7, 8, 9, 10, 11, 12, 13, 14, or 15 mm from a distal end of the outer sheath 102.

Any number of different surgical instruments 452 can be used. For example, FIG. 6 shows a suction instrument 454, a cautery instrument (such as a bipolar cautery instrument) 456, and scissors 458. However, other instruments can be used as well, such as, for example micrograsping forceps, microscissors, a microdissector, a cautery instrument, a suction device, a vessel clip, a ligation instrument, a drug delivery device, an ultrasonic or microdoppler flow probe, and a spectroscopy probe. In some embodiments, not every strut 402 has a surgical instrument 452, such as shown in FIG. 6. In some embodiments, every strut 402 has a surgical instrument 452. In some embodiments, each surgical instrument 452 is different. In some embodiments, the struts 402 are the surgical instruments themselves (e.g., no lumen extending through the struts 402). In some embodiments, two or more of a certain surgical instruments 452 can be used. The surgical instruments 452 can be connected at their proximal end to different devices that can operate the surgical instruments 452, such as a power source, and electrical source, a suction source, a mechanical operation source, etc. The surgical instruments 452 and struts 402 may include flexible portions to bend along with the device 100.

Designs are contemplated by which circumferentially opposing struts 402 and surgical instruments 452 are placed strategically across from each other to oppose one another within a circular, hexagonal or octagonal arrangement and thereby maintain maximal dilation of tissue. Similarly, the device 100 may be designed to less preferentially have surgical instruments 452 which frequently co-function be located adjacent to one another.

In some embodiments, the surgical instruments 456 can have modular instrument functions in any combination of the following: suction device (with or without retractable sharp dissector or knife), single shaft micro-scissors, single shaft micro-grasping forceps, dissector, curette, drug delivery or irrigation cannula, ultrasonic probe, optical probe for spectroscopy or OCT, vascular clip applier for vessels or aneurysms, ligation devices, monopolar, sesquipolar, or bipolar cautery, endoluminal access device, electrophysiological stimulation probe, drill or ultrasonic curette, ultrasonic aspirator, or side cutting aspirator. Other instruments can be used as well, and the type of instrument is not limiting. In some embodiments, the surgical instruments 456 can be removed and replaced for different instruments during a procedure. In some embodiments, the surgical instruments 456 can be removed and replaced for different instruments between procedures.

At any time during an operation, the struts 402 and surgical instrument 452 can be withdrawn back into the outer sheath 102, and simultaneously converge or collapse back together, thereby forming a grasping "claw" which can be used to trap and remove surgical tissue (e.g., a tumor). The synchronized motion of struts 402 for the formation of a claw may be automatically controlled robotically.

The surgical instruments 452 can be controlled by a human or robot, and can be advanced from the outer sheath 102 to expand the canopy 500 and dock on the surgical target.

Each strut 402 and/or surgical instrument 452 may be hinged, motorized, and independently maneuverable via a human or robot to facilitate surgical manipulation, dissection, cutting, resection or cautery of tissue. Struts 402 and/or surgical instruments 452 may be automatically controlled during manipulation and able to follow trajectories or maintain regulated fixed positions. In some embodiments, the hinges, bends, or "elbows" of the struts 402 maintain tissue retraction while the distal ends simultaneously perform primary surgical functions at the surgical instruments 452. In some embodiments, information from each instrument 452, such as via actuators or additional sensors, may be relayed (via wires or otherwise) back to the proximal robotic device or central processing unit, so as to provide information/data including instrument location/coordinates, temperature, sensor information from ultrasonic or spectroscopic sensors, haptic feedback, pressure sensors, optical sensors, tissue resistance/pressure, impedance, current, etc. This information may then be integrated into software feedback algorithms which can manually, robotically or otherwise automatically regulate or control the performance or function of each instrument.

In some embodiments, only some of the struts 402 perform surgical operation. Thus, some of the struts 402 (e.g., nonworking struts) remain radially outwards to continue forming the canopy 500 while other struts (e.g., working struts) extend more radially inward to perform the operation using the surgical instruments 452. The struts with the surgical instruments 452 may continue forming the canopy 500 in some embodiments. In some embodiments, the struts 402 with the surgical instruments 452 may no longer be a part of the canopy, leaving the remaining struts 402 to hold the canopy. In some embodiments, 2, 3, 4, 5, 6 struts 402 can be nonworking struts. In some embodiments, greater than 2, 3, 4, 5, 6 struts 402 can be nonworking struts. In some embodiments, less than 2, 3, 4, 5, 6 struts 402 can be nonworking struts. In some embodiments, 1, 2, 3, 4, 5, 6 struts 402 can be working struts. In some embodiments, greater than 1, 2, 3, 4, 5, 6 struts 402 can be working struts. In some embodiments, less than 2, 3, 4, 5, 6 struts 402 can be working struts.

Figure 7:
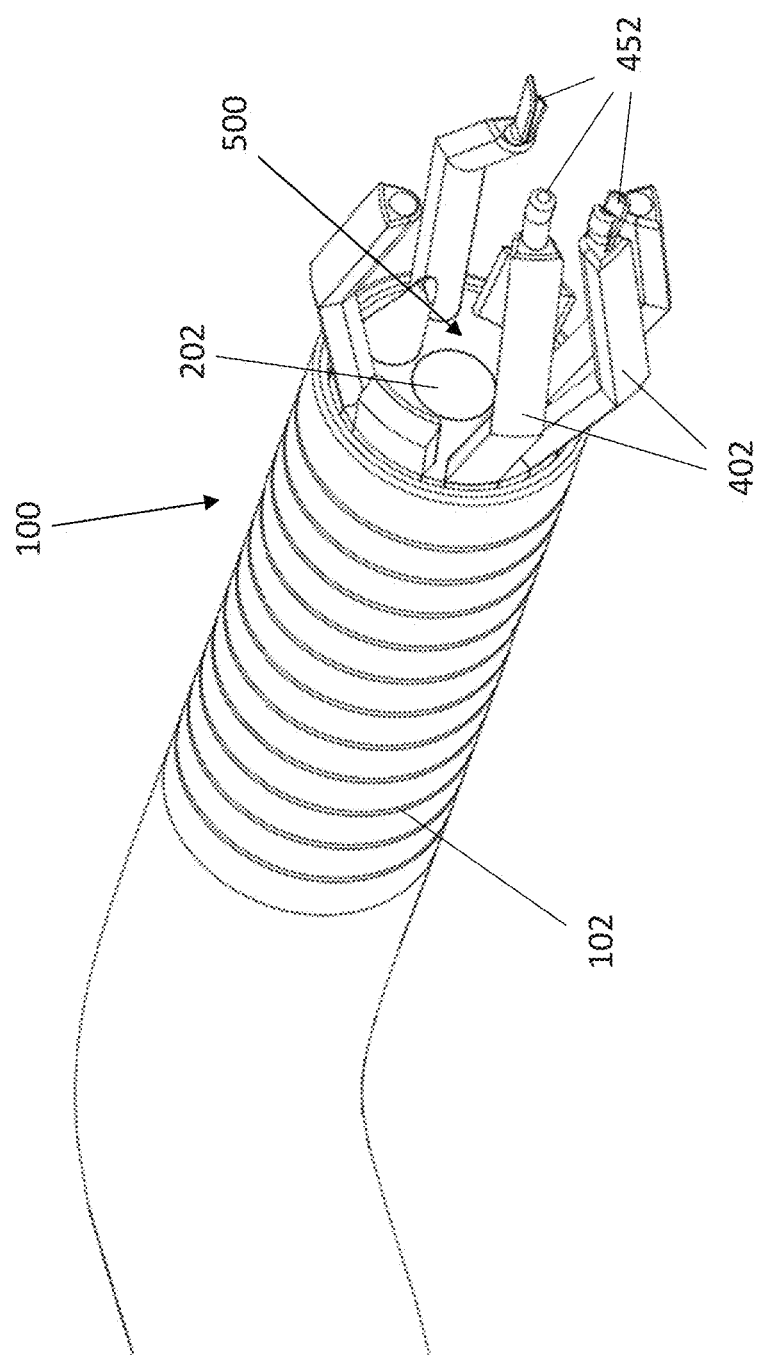
FIG. 7 illustrates an embodiment of the end effectors of the struts distally extended.

FIG. 7 illustrates the device 100 and canopy 500 with the surgical instruments 452 deployed.

Figure 8:
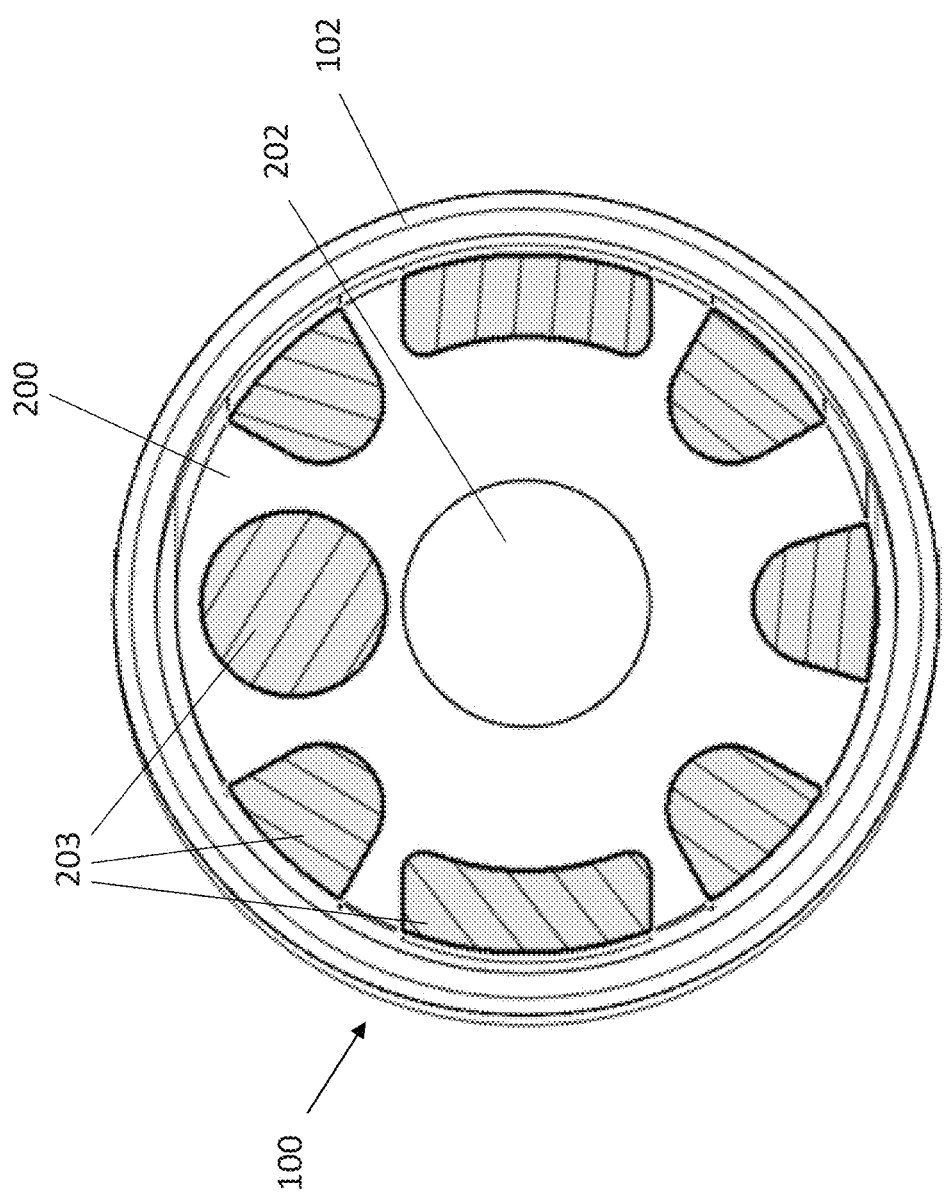
FIG. 8 illustrates a head on view of an embodiment of the surgical device.
Figure 9:
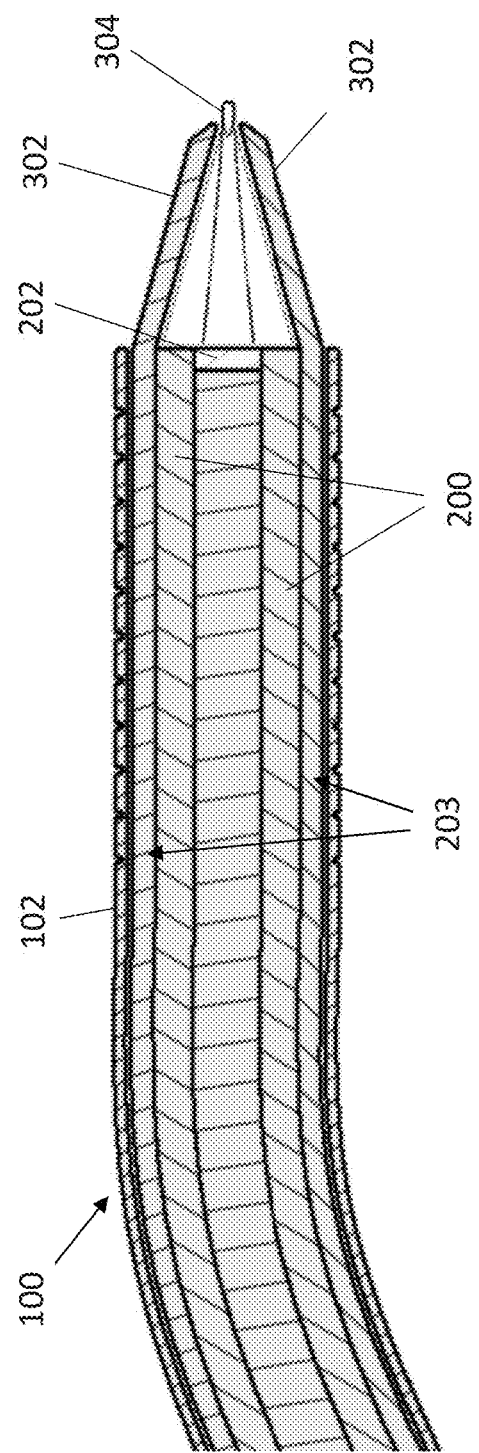
FIG. 9 illustrates a cross-section of an embodiment of the surgical device.

FIG. 8 illustrates a head-on view of the distal end of the device 100. As shown, the inner module 200 can contain a number of lumens 203 for extension of the different components discussed above. For example, there can be a lumen for the legs 302, needle 304, struts 402, and visualization device 202. The distal end of the lumens 203 can be "sealable" to provide fluid or tissue from entering them. For example, each of the lumens 203 can have a seal over them. FIG. 9 illustrates a cross-section of the distal end of the device 100.

Figure 10A:
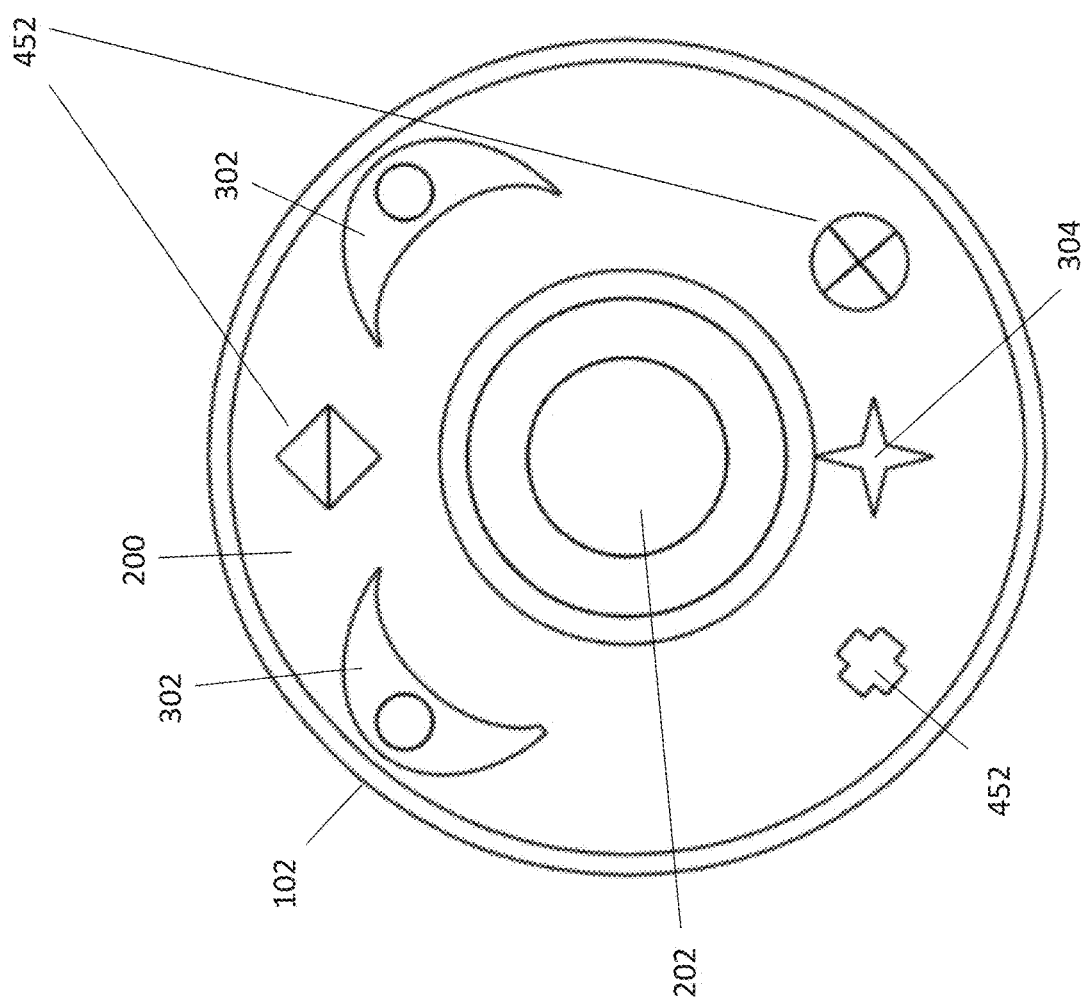
FIGS. 10A and 10B illustrate schematic examples of distal end of embodiments of a surgical device with certain structurers omitted for convenience.
Figure 10B:
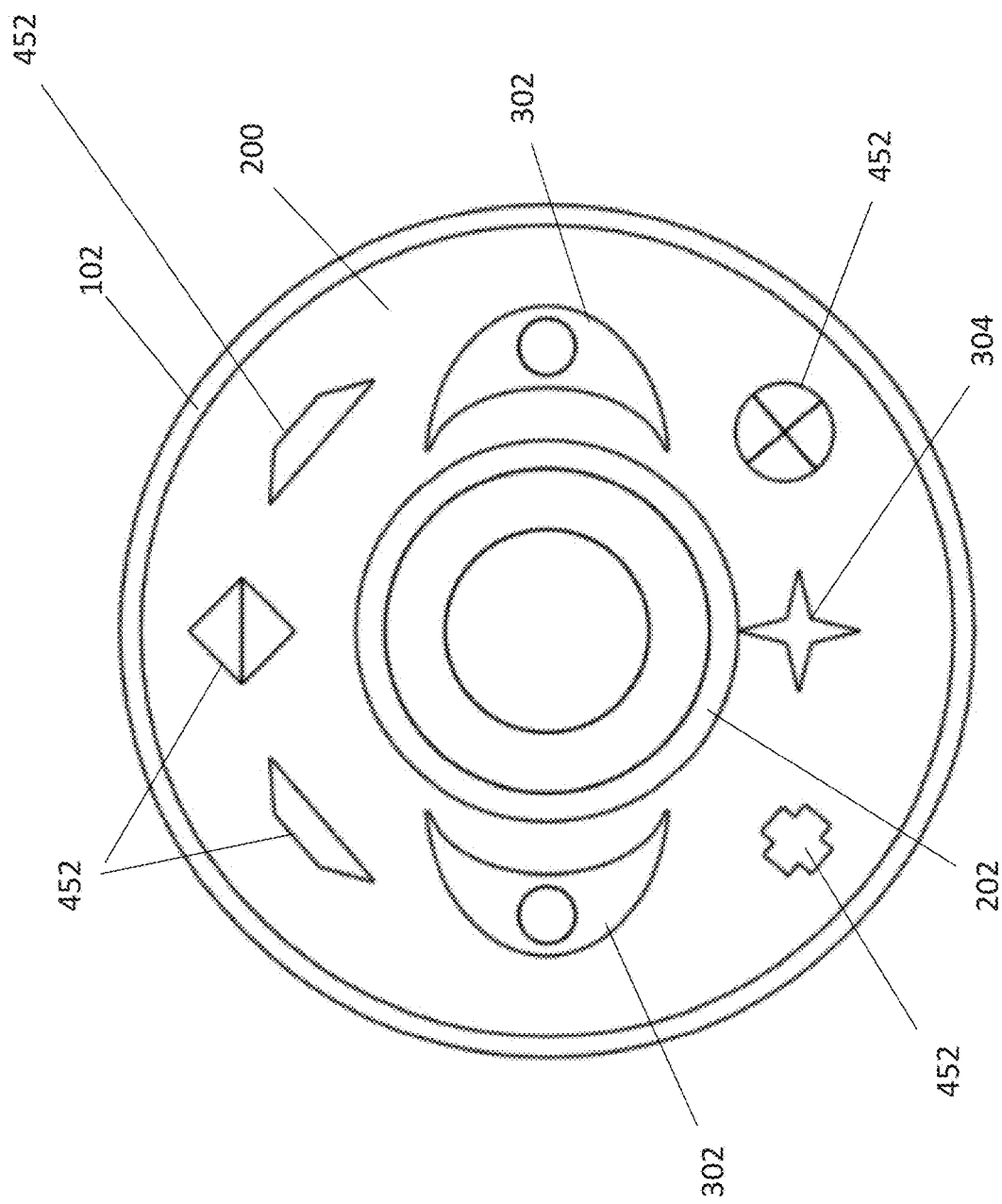
Figure 11:
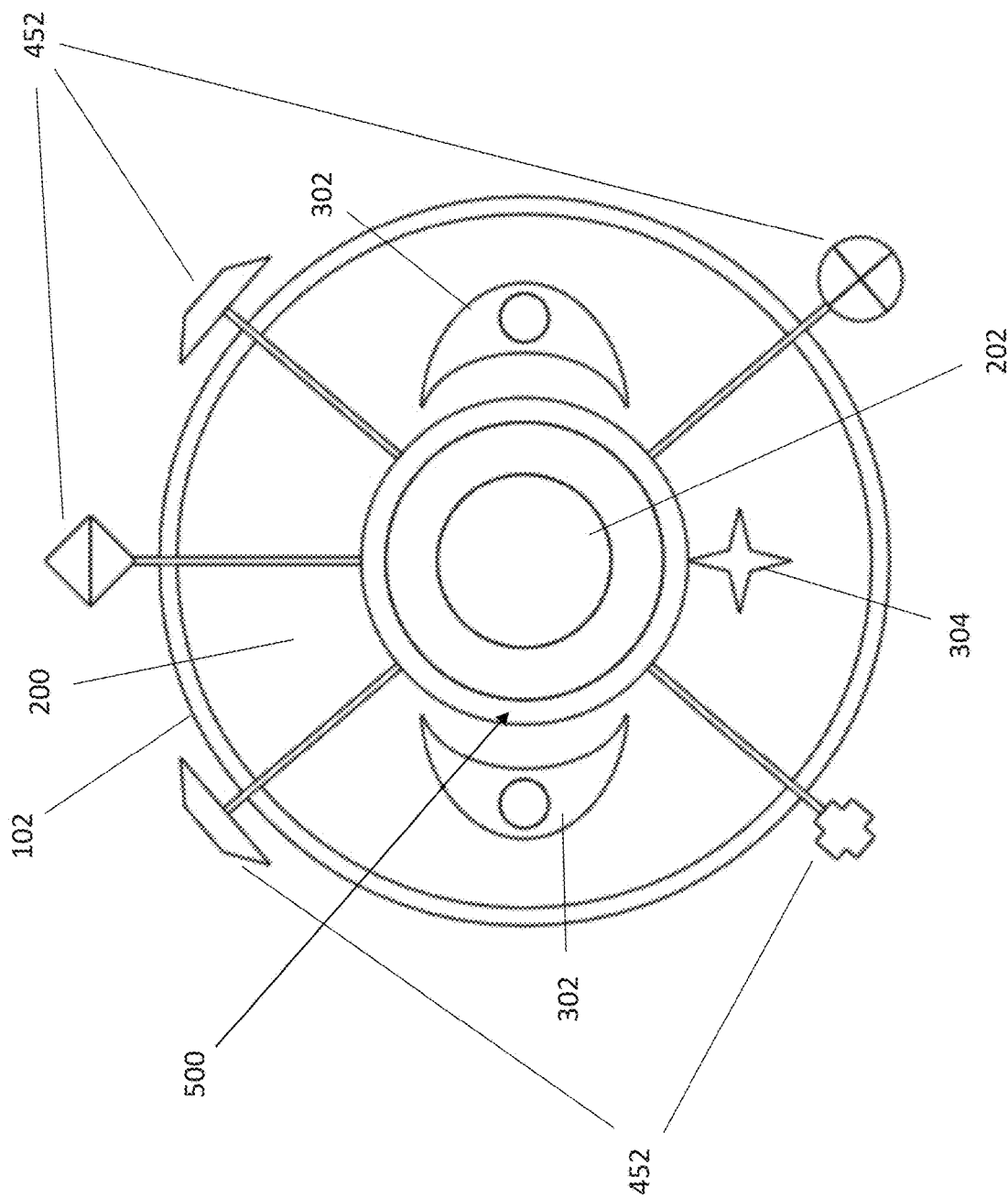
FIG. 11 illustrates a schematic example of a distal end of an embodiment of the surgical device showing the formation of the working canopy with certain structurers omitted for convenience.

FIGS. 10A, 10B, and 11 illustrate a schematic example of device 100 showing relative distalmost positions of certain components within the device 100. Certain structural elements (and portions of other shown structural elements) are omitted for convenience. Thus, the particular shape of the device 100 and related components shown is not limiting.

FIGS. 10A-10B illustrates a front-end view of the distal end of the device 100 with different amounts of struts 402 and surgical instruments 452. The particular shape of the distal end of the surgical instruments 452 in FIGS. 10A-10B is not representative of the actual shapes of the surgical instruments 452.

FIG. 10B shows five surgical instruments 452 attached to the struts 402 in the retracted position (e.g., withdrawn into the outer sheath 102) while FIG. 11 shows the five surgical instruments 452 attached to the struts 402 in the extended position (e.g., distally extending from outer sheath 102). As shown, the surgical instruments 452 extend (e.g., dilate) circumferentially outwards when extending distally from the outer sheath 102. This allows the canopy (or workspace) 500 to form between the surgical instruments 452, as shown in FIG. 11, allowing for a user to operate within the canopy 500. The particular shape of the distal end of the surgical instruments 452 in FIG. 11 is not representative of the actual shapes of the surgical instruments 452.

The device/system 100 discussed above and any or all of its components can be operated by a user and/or a robot (such as a robotic arm) and/or a computer. In some embodiments, certain functions can be done automatically. The device 100 can be used in conjunction with other imaging equipment in some embodiments.

While the above disclosure discusses a surgical device 100 which includes both the labrum 300 in combination with the struts 402 forming the canopy 500, in some embodiments these may be two separate devices. For example, an initial (or first) device can include just the outer sheath 102 and labrum 300, which may or may not be retractable into the device. It may further include the inner module 200 discussed above. This device can allow access to a target tissue. A second device may then include the canopy forming struts 402 in an outer sheath 102. It may further include the inner module 200 discussed above. Thus, the first device may look like FIG. 1 and the second device may look like FIG. 7. In some embodiments, the first device may contain a lumen for the second device to be inserted through.

In some embodiments, the same outer sheath 102 can be used for the first device and the second device. For example, a first inner module can contain the labrum 300. Once used, the first inner module can be removed from the outer sheath 102. A second inner module containing the struts 402 can then be inserted into the same outer sheath 100. In some embodiments, the same inner module is used as well, and the labrum can be withdrawn from the device and the struts can be inserted into them.

Method of Use

FIGS. 12-18 show an example embodiment of a method of use of the device 100 in tissue 600 in order to interact with target tissue 602. FIGS. 13-18 illustrate a cross-section of the device 100 for clarity.

Figure 12:
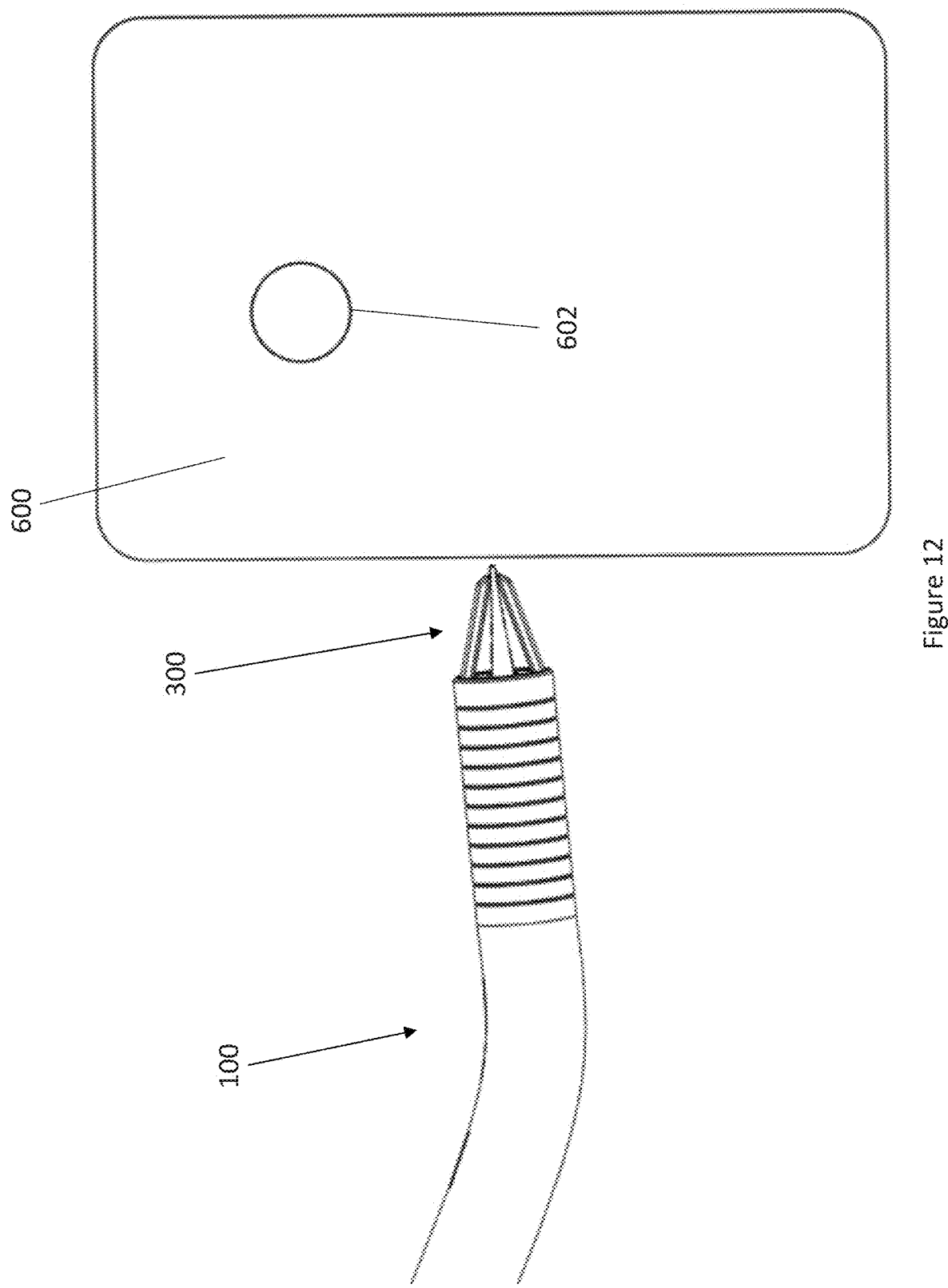
Figure 13:
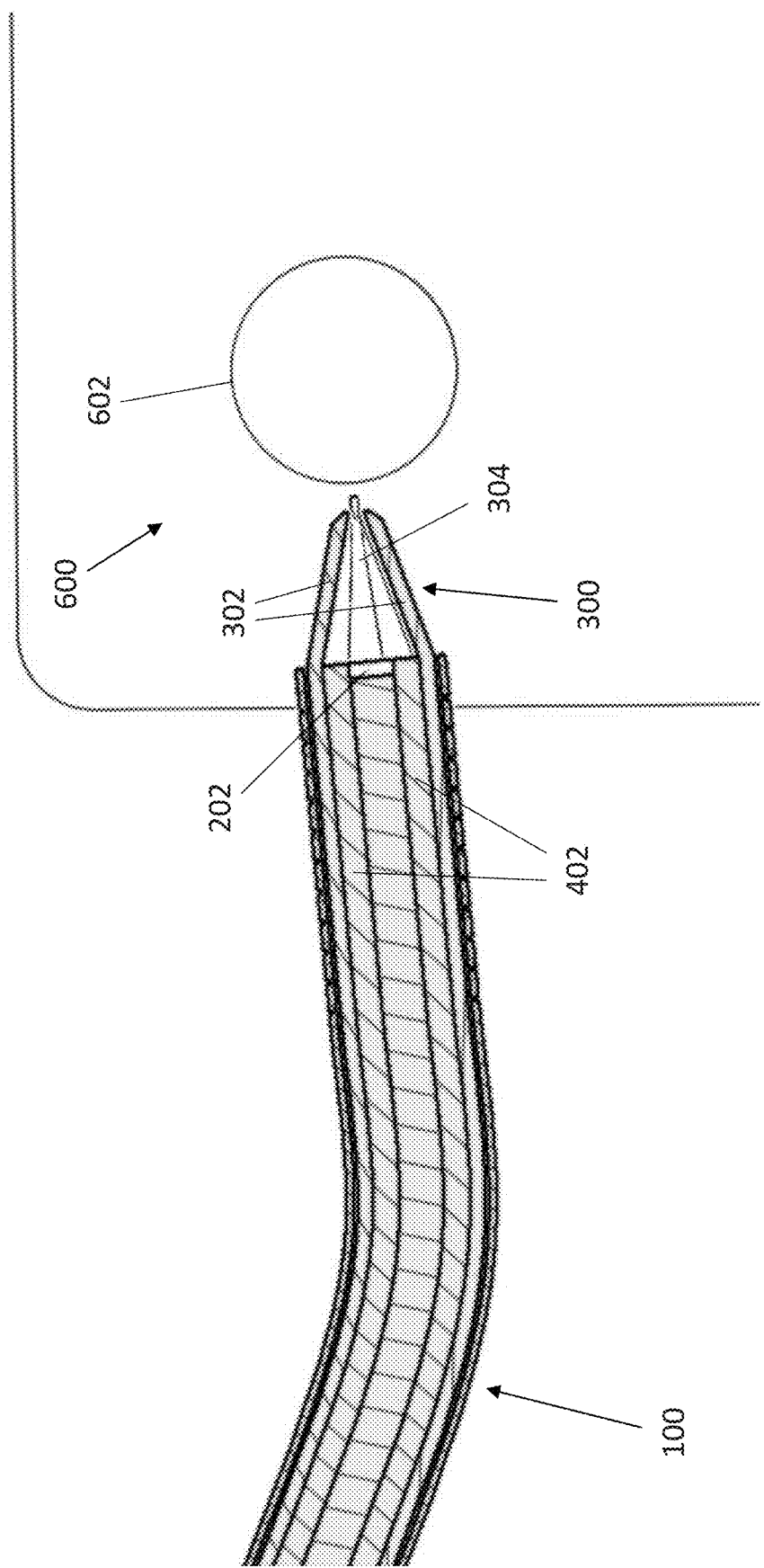

As shown in FIG. 12, the device 100 can start outside of tissue 600. As discussed above, the labrum 300 can pierce into the tissue 600, such as shown in FIG. 13. In some embodiments, the device 100 may be used via a small percutaneous incision and/or burr hole to access a target tissue 602 using navigation, direct or indirect visualization via a camera or endoscope, and/or ultrasonic probe, pressure, or LED sensor. The labrum 300 (e.g., the arms 302 and needle 304) can radially open and close as the device 100 moves through the tissue to cut and move tissue out of the way as the device 100 is maneuvered towards the target tissue 602. The labrum 300 can be used to swiftly penetrate soft tissue and maneuver the outer sheath 102 to the target with minimal tissue disruption as a mosquito does. In some embodiments, the labrum 300 vibrates rapidly in and out of the sheath to provide a cutting effect of soft tissue as the labrum 300 advances, as occurs with a mosquito proboscis.

The device 100 can be steered manually or robotically through the tissue 600. In some embodiments, the device 100 is steered like an endoscope. In some embodiments, the device 100 may contain pull wires for steering. In some embodiments, the device 100 may include ratcheting mechanisms for steering.

Figure 14:
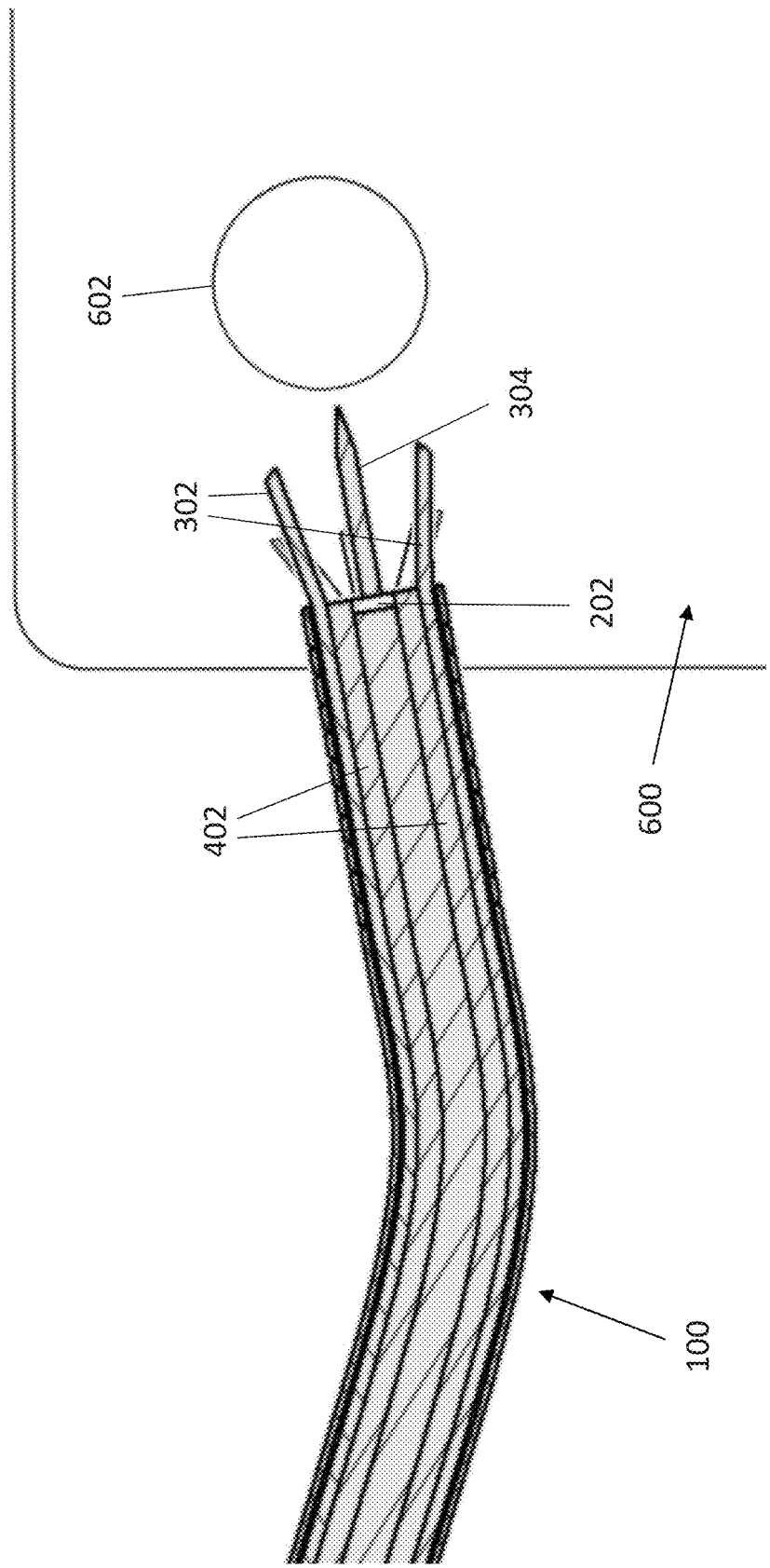

Once at or near the target tissue 602 (e.g., upon "docking" immediately superficially), the labrum 300 can be withdrawn into the outer sheath 102 and/or module 200 of the device 100. Further, struts 402 can extend distally outwards as shown in FIG. 14. The labrum 300 can be withdraw prior to the struts 402 distally extending or simultaneously with the struts 402 distally extending. In some embodiments, the labrum 300 is not withdrawn.

Figure 15:
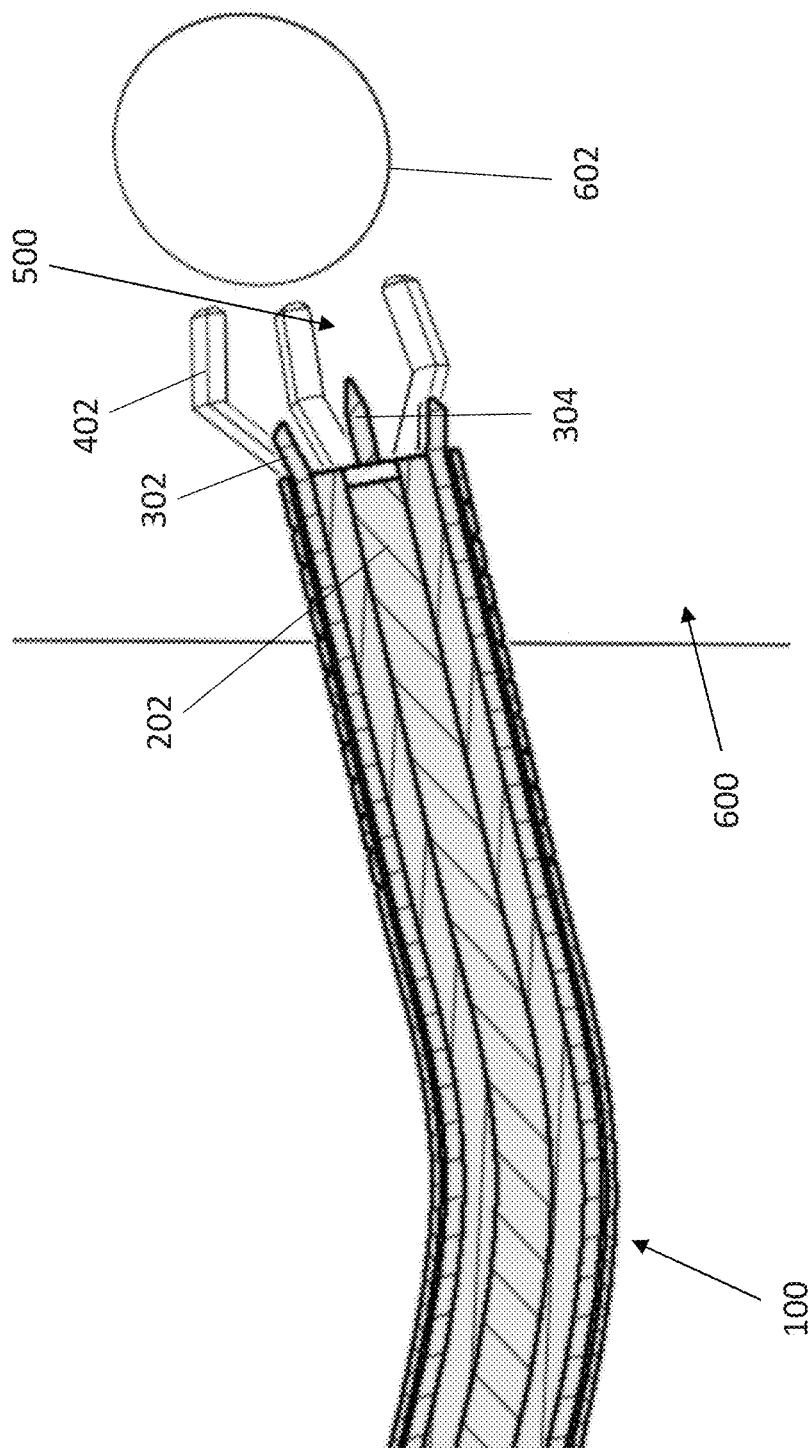

As shown in FIG. 15, the struts 402 can continue to advance both circumferentially outwards and distally to begin forming the canopy 500 so that a user can see the target tissue 302, such as using a visualization device 202. The expanding struts 402 can further move tissue out of the way in order to form a working area in the canopy 500.

Figure 16:
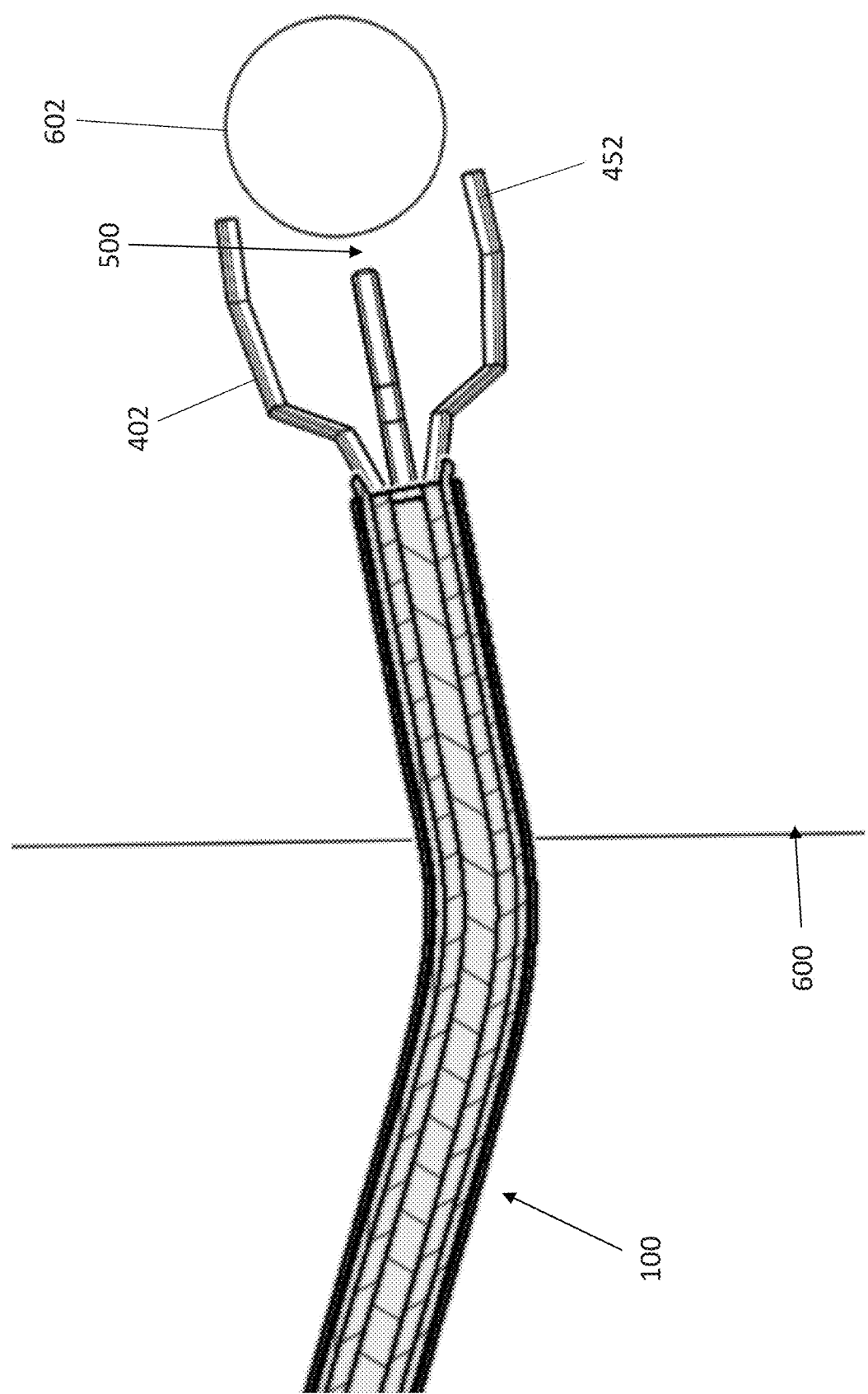

FIG. 16 shows the struts 402 in the fully expanded position forming the canopy 500. At this time, the surgical instruments 452 may extend from the struts 402 in order to manipulate target tissue 602. In some embodiments, the surgical instruments 452 have previously been extended distally.

The surgical instruments 452 may be manipulated by a human or robot located at the proximal end or remotely. The surgical instruments 452 may be controlled robotically via teleoperation or via autonomy, or semi-autonomy. Teleoperation can be telefunctional in nature wherein a non-identity transformation can be present from the master to slave. Teleoperation can occur with or without haptic feedback, either during surgical functions or during solely user interface functions. The surgical instruments 452 motions may be actuated via tendon driven or concentric tube architectures, without limitation.

Figure 17:
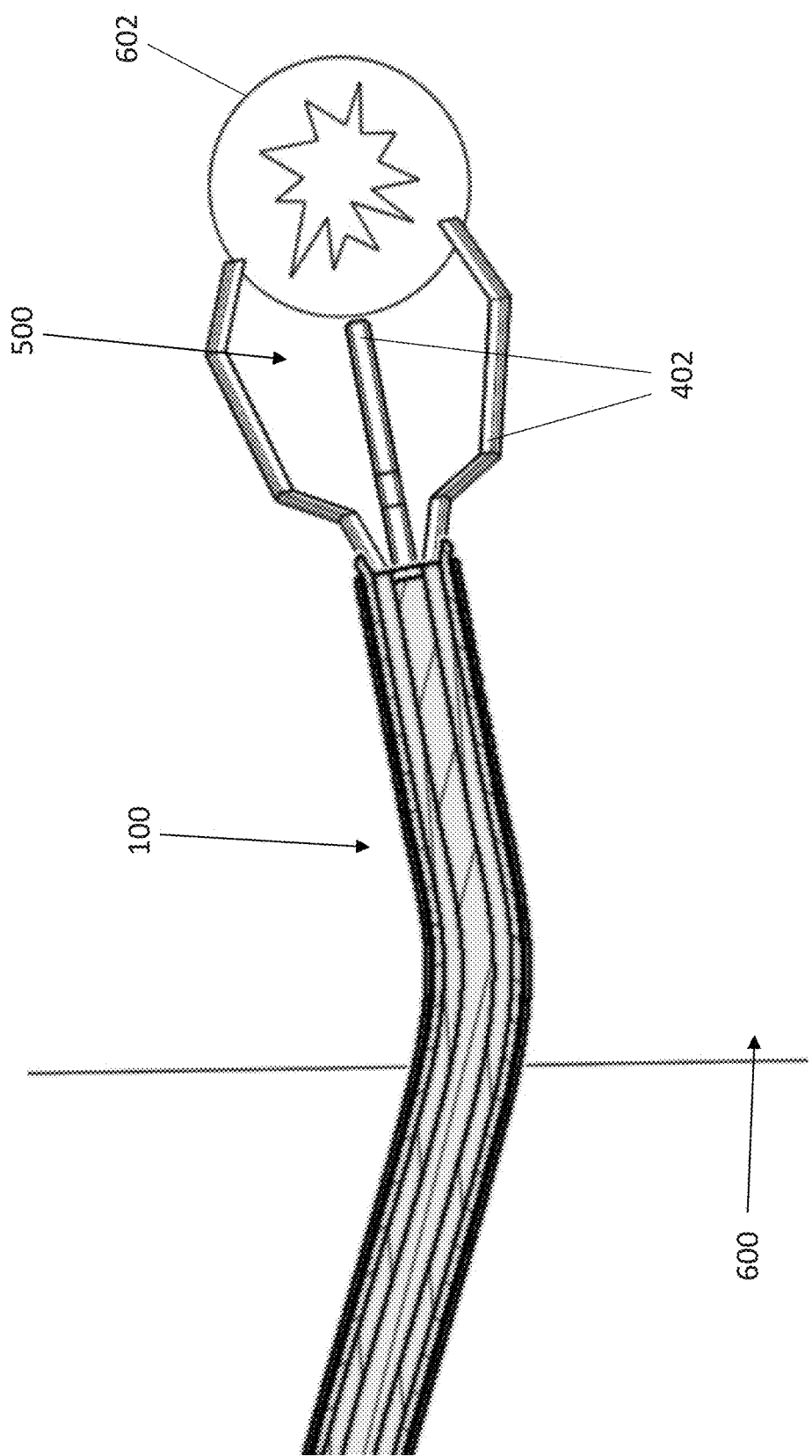

FIG. 17 shows the struts 402 manipulating the target tissue 602. This can include cutting, cauterizing, cooling, suction, grasping as discussed above. In the embodiment shown in the figures, the struts 402 can form a grasping "claw" in order to remove the target tissue 602, such as if the target tissue was a tumor or other removable tissue. In some embodiments, some of the struts 402 form the grasping claw while others perform other tissue manipulation.

So as to maintain tissue retraction and the canopy effect provided by the previously described struts 402, in some embodiments only some struts 402 (for example, only up to three or four strut instruments) may converge at the target tissue 602 and interact in unison or independently at any given time on target tissue 602. These "working" struts 402 may be rigid, angled, curved or hinged. They can interact near the center and distally to the working channel at the target zone under the canopy 500 provided by the "non-working" struts. In combination, they may be used to perform any number of surgical functions based on the instrument functions listed above. This provides and maintains a visible workspace within tissue provided by the dilatory and retraction effect of the struts used to create a surgical canopy 500.

FIG. 18 illustrates the target tissue 602 withdrawn to the distal end of the outer sheath 102. The device 100 can then be removed from the tissue 600.

If a two device embodiment discussed above is used, the first device can be inserted into tissue to form a tunnel and withdrawn. The second device (or the same outer sheath with new internal components) can be inserted into the leftover tunnel in the tissue to perform a surgical operation on the target tissue.

In some embodiments, the second device can fit within a lumen of the first device. Thus the first device can access the target tissue and once located in the proper position, the second device can be inserted through the first device to perform an operation on the target tissue.

The devices, systems and methods described herein can be used to access deep surgical targets via percutaneous or minimally invasive corridors, including burr holes or small keyhole incisions. It can be used to remove tumors, perform biopsies, fenestrate cysts, access blood vessels (much like a mosquito), and clip aneurysms without the need for an open approach (e.g. craniotomy) or major tissue retraction to access the target (e.g. brain retractors).

From the foregoing description, it will be appreciated that inventive surgical systems are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A multi-functional surgical system comprising:
   an outer sheath having a proximal end, a distal end, and a lumen extending between the proximal end and the distal end;
   a labrum extending through the outer sheath and configured to extend out the distal end of the outer sheath, the labrum comprising a cutter configured to penetrate tissue and a plurality of legs configured to move from a radially closed position to a radially open position to move tissue in an outward direction; and
   a plurality of struts that can be longitudinally retracted into the outer sheath and longitudinally extended distal to the outer sheath.

2. The multi-functional surgical system of claim 1, further comprising an inner module located within the lumen of the outer sheath, the inner module comprising a plurality of lumens extending from a proximal end to a distal end of the inner module, wherein the outer sheath and the inner module are flexible.

3. The multi-functional surgical system of claim 2, further comprising a camera or endoscope extending through one of the plurality of lumens of the inner module.

4. The multi-functional surgical system of claim 2, wherein the labrum is configured to withdraw into at least one of the plurality of lumens of the inner module.

5. The multi-functional surgical system of claim 1, further comprising a hub and relay connected to a processor with a human or robotic interface.

6. The multi-functional surgical system of claim 1, further comprising a power source connected to the labrum and/or the plurality of struts.

7. The multi-functional surgical system of claim 1, wherein the plurality of struts are configured to form a grasping claw while being withdrawn into the outer sheath.

8. The multi-functional surgical system of claim 1, further comprising one or more of a micrograsping forcep, a microscissors, a navigation actuatuator, a microdissector, a cautery instrument, a suction device, a vessel clip, a ligation instrument, a drug delivery device, an ultrasonic or micro-doppler flow probe, and a spectroscopy probe.

9. The multi-functional surgical system of claim 1, wherein at least a portion of the labrum is configured to vibrate.

10. The multi-functional surgical system of claim 1, wherein the system is bendable and steerable.

11. The multi-functional surgical system of claim 1, wherein each of the plurality of struts comprises a bend, the bend directing the strut from extending radially outward to extending radially inwards.

12. The multi-functional surgical system of claim 11, wherein the bend comprises a hinge configured to change angles.

13. The multi-functional surgical system of claim 1, wherein at least one of the plurality of struts comprise a surgical end tip having a surgical function.

14. A method of performing surgery comprising:
    advancing the multi-functional surgical system of claim 1 to a target location with a target tissue, the advancing comprising cutting through tissue with the labrum of the surgical system to enter the target location;
    distally advancing the plurality of struts through the outer sheath and into the target location, wherein the plurality of struts radially expand as they are distally advanced out of the outer sheath to form a canopy working area around the target tissue and wherein at least one of the plurality of struts include an end effector; and
    performing an action on the target tissue using at least one of the end effectors of the plurality of struts.

15. The method of claim 14, wherein the performing the action comprises cutting, cauterizing, dissection, clipping, ligation, drug delivery, suction, removal, or grasping.

16. The method of claim 14, wherein the surgical system is controlled robotically.

17. The method of claim 14, further comprising retracting the labrum into the outer sheath prior to or simultaneously while distally advancing the plurality of struts.

18. The method of claim 14, further comprising withdrawing the plurality of struts after performing the action, wherein the withdrawing comprises radially compressing the plurality of struts to grasp the target tissue and translate the target tissue towards the outer sheath.

19. The assembly of claim 1, further comprising an inner module located within the lumen of the outer sheath, the inner module comprising a plurality of lumens extending from a proximal end to a distal end of the inner module.

20. The assembly of claim 1, wherein the second surgical device extends through at least one of the plurality of lumens.

21. An assembly for a surgical system, the assembly comprising:
    a first surgical device comprising a labrum at a distal end of the surgical system, the labrum comprising a pair of legs each having a cutting edge at a distal end thereof and a tissue cutter configured to form a unified dissector to penetrate tissue and to move from a radially closed position to a radially open position to move tissue in an outward direction;
    wherein:
       a body portion of the tissue cutter is positioned between at least a distal portion of the legs of the plurality of legs when the plurality of legs are in the radial open position; and
       the tissue cutter extends further in a distal direction than the distal ends of the pair of legs so that the tissue cutter acts as the initial tissue cut or penetration point when the labrum is advanced in a distal direction.

22. A method of using the assembly of claim 21, the method comprising:
    advancing the first surgical device near to a target tissue to form a tunnel;
    withdrawing the first surgical device through the tunnel;
    advancing a second surgical device through the tunnel; and
    performing a surgical operation with the second surgical device.

23. The assembly of claim 21, further comprising a second surgical device comprising at least one of a plurality of struts, a suction device, an endoscope, a tissue cutter, and an aspirator.

24. The assembly of claim 21, wherein the tissue cutter is a needle.

25. The assembly of claim 21, wherein the pair of legs are configured to move from the radially closed position to the radially open position to move tissue and to form a canopy working area.

26. The assembly of claim 21, wherein the pair of legs and the tissue cutter of the labrum are advanceable through a lumen of the first surgical device.

27. A surgical system comprising:
    an outer sheath;
    a unified tissue dissector extending through the outer sheath comprising a tissue cutter and a plurality of legs, the tissue cutter and/or plurality of legs of the unified tissue dissector being configured to extend past a distal end of the outer sheath to penetrate into tissue, and the plurality of legs being configured to radially open and close to retract tissue radially outwardly to facilitate advancement of at least a portion of the surgical system through soft tissue; and a second surgical device configured to be advanced from within the outer sheath, the second surgical device configured to perform a second function at the surgical target site;

wherein:

at least a portion of the unified tissue dissector and at least a portion of the second surgical device are coaxially positioned relative to one another; and the second surgical device is configured to be extended distally past the distal end of the outer sheath at least when the unified tissue dissector is extended distally past the distal end of the outer sheath such that both the unified tissue dissector and the second surgical device can be extended past the distal end of the outer sheath at the same time.

28. The surgical system of claim 27, wherein the second surgical device comprises a plurality of struts, a suction device, an endoscope, a tissue cutter, or an aspirator.

\* \* \* \* \*